(12) United States Patent
Uenaka et al.

(10) Patent No.: US 6,831,177 B1
(45) Date of Patent: Dec. 14, 2004

(54) PROCESSES FOR THE PREPARATION OF SUBSTITUTED PROPENONE DERIVATIVES

(75) Inventors: Masaaki Uenaka, Osaka (JP); Kyozo Kawata, Amagasaki (JP); Masahiko Nagai, Osaka (JP); Takeshi Endoh, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 24 days.

(21) Appl. No.: 09/980,578

(22) PCT Filed: May 29, 2000

(86) PCT No.: PCT/JP00/03456

§ 371 (c)(1),
(2), (4) Date: Dec. 3, 2001

(87) PCT Pub. No.: WO00/75122

PCT Pub. Date: Dec. 14, 2000

(30) Foreign Application Priority Data

Jun. 2, 1999 (JP) .......................................... 11/155503
Aug. 17, 1999 (JP) .......................................... 11/230305

(51) Int. Cl.$^7$ .......................................... C07D 249/10
(52) U.S. Cl. .................................. 548/266.6; 548/266.8
(58) Field of Search ........................... 548/266.6, 266.8

(56) References Cited

U.S. PATENT DOCUMENTS

| | | | |
|---|---|---|---|
| 5,759,842 A | 6/1998 | Dombrowski et al. | 435/252.1 |
| 6,333,323 B1 | 12/2001 | Fujishita et al. | 514/233.5 |

FOREIGN PATENT DOCUMENTS

| | | |
|---|---|---|
| GB | 1481990 | 8/1977 |
| GB | 2 271 566 | 4/1994 |
| GB | 2 306 476 | 5/1997 |
| JP | 52-68182 | 6/1977 |
| JP | 61-53275 | 3/1986 |
| JP | 7-78056 | 8/1995 |
| JP | 7-78057 | 8/1995 |
| WO | 96/40255 | 12/1996 |
| WO | 98/34932 | 8/1998 |
| WO | 99/50245 | 10/1999 |
| WO | 2000/39086 | of 2000 |

OTHER PUBLICATIONS

Chemical Abstracts, vol. 108, 1988, Abstract No. 204566x.
T. Vanek et al., "Preparation of 3– And 3,5–Substituted 1,2,4–Triazoles", Collect. Czech. Chem. Commun., 49, pp. 2492–2495, 1984.
Heterocyclic Compounds, vol. 70, pp. 344–345, 1969, 77876t.
Heterocyclic Compounds, vol. 64, pp. 5073–5074, 1966.
J. Am. Chem Soc., vol. 76, p. 291, 1954.
N. Bozhkova et al., "Synthesis of 4–Alkoxy–1, 3–oxazol–5(2H)–ones, Precursors of 1–Alkoxy–Substituted Nitrile Ylides", Helvetica Chimica Acta., vol. 72, pp. 825–837, 1989.
Chem. France, pp. 1166–1171, 1962.
Khim, Geterotsikl. Soedin, pp. 624–627, 180, 1967.
Khim. Geterotsikl. Soedin, pp. 180–183, 624, 1965.
F.G. De Las Heras et al., "Synthesis and cytostatic and trichomonacide activities of 1–glucosyl–nitro–1,2,4–triazoles", Eur. J. Med. Chem Chim. Ther., vol. 19, No. 1, pp. 89–92, 1984.
P. Vemishetti et al., "The preparation of 2'–Deoxy–2'–fluoro–1',2'–seconucleosides as potential antiviral agents", Journal of Medicinal Chemistry, vol. 33, No. 2, pp. 681–686, 1990.
P. vemishetti et al., "A practical synthesis of ethyl 1,2, 4–triazole–3–carboxylate and its use in the formation of chira 1',2'–seco–nucleoties of ribavirin (1)", J. Heterocycl. Chem., vol. 25, No. 2, pp. 651–654, 1988.
H. Gilmann et al., "Super–Aromatic Properties of Furan. II. The Friedel–Crafts Reaction", J. Am. Chem. Soc., vol. 55, pp. 4197–4200, Oct. 1933.

*Primary Examiner*—Fiona T. Powers
(74) *Attorney, Agent, or Firm*—Wenderoth, Lind & Ponack, L.L.P.

(57) ABSTRACT

Industrial and commercial processes for the preparation of 2-acyl-5-benzylfuran derivatives, 1,2,4-triazole-3-carboxylic acid ester derivatives or propenone derivatives having an anti-HIV activity; and useful crystals of the derivatives. A deblocking: (III-2), (IV-10), (VI-1), wherein $R^1$, $R^2$ and $R^4$ are each independently hydrogen or the like; A is $CR^6$ or N; $R^6$ is hydrogen or the like; Q is a protecting group; and L is a leaving group.

9 Claims, 9 Drawing Sheets

PROCESSES FOR THE PREPARATION OF SUBSTITUTED PROPENONE DERIVATIVES

This application is a 371 of PCT/JP00/03456 filed May 29, 2000.

TECHNICAL FIELD

The present invention relates to processes for the preparation of novel substituted propenone derivatives and their crystals, in detail processes for the preparation of their intermediates, 2-acyl-5-benzylfuran derivatives and 1,2,4-triazole-3-carboxylic acid ester derivatives.

BACKGROUND ART

2-Acyl-5-alkylfuran derivatives, which are similar to 2-acyl-5-benzylfuran derivatives, can be prepared by introducing an acyl group to 2-alkyfuran derivatives through Friedel Crafts reaction (Japanese Patent Publication (Kokoku) 1995-78056, Japanese Patent Publication (Kokoku) 1995-78056 and Japanese Patent Publication (Kokai) 1986-53275).

2-Alkylfuran derivatives can be prepared by introducing an alkyl group to furan derivatives through Priedel Crafts reaction (Chem. France. 1962, 1166).

However, the preparation of 2-acyl-5-benzylfuran derivatives is not disclosed in these documents.

On the other hand, it is known that 1,2,4-triazole-3-carboxylic acid can be prepared by converting an amino group of 3-amino-1,2,4-triazole-5-carboxylic acid to a diazo group, isolating the diazonium salt and reducing.

It is known as a reducing method that 1) a diazonium salt is reduced with sodium hypophosphite ($NaH_2PO_2$) and concentrated hydrochloric acid (HCl) under 15° C. (Khim. Geterotsikl. Soedin., 1967, 180–183) and 2) a diazonium salt is reduced at 45 to 50° C. in methanol (Khim. Geterotsikl. Soedin., 1965, 624–626).

In is known as a deaminating method of 3-amino-1,2,4-triazole that diazonation and reduction are carried out at the same time (J. Am. Chem. Soc. 76, 290, 1954).

As another process, 1,2,4-triazole-3-carboxylic acid ester can be prepared by heating acylamidrazone over its melting point (150 to 200° C.) to cyclize (Collect. Czech. Chem. Commun., 49, 1984, 2492–2495, J. Heterocyclic Chem., 25, 651–654, 1998). The document describes that a large scale of cyclization must be preformed under reduced pressure with heating over its melting point for removing the generated water.

DISCLOSURE OF INVENTION

A compound of the formula (VI-1):

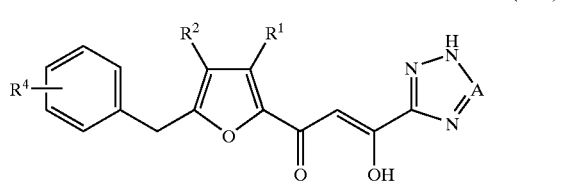

(VI-1)

wherein $R^1$, $R^2$ and $R^4$ each is independently hydrogen, optionally substituted alkyl, optionally substituted alkoxy or halogen; A is $CR^6$ or N; and $R^6$ is hydrogen, optionally substituted alkyl or optionally substituted aryl, has an anti-HIV activity by inhibiting HIV integrase.

A compound of the formula (VI-1) can be prepared in the following method.

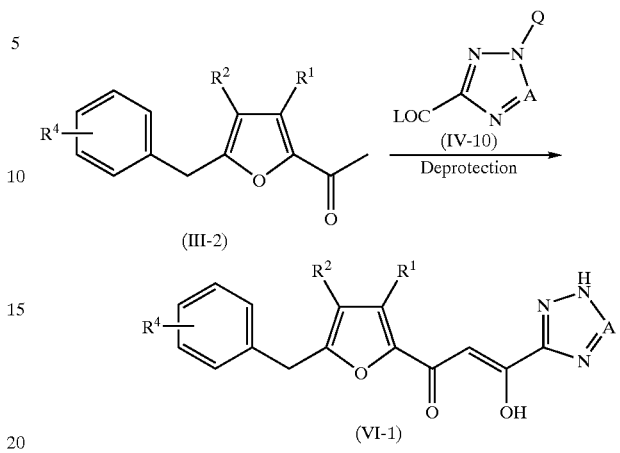

wherein $R^1$, $R^2$, $R^4$ and A are as defined above; Q is a protecting group; and L is a leaving group.

Industrial and commercial preparations of 2acyl-5-benzylfuran derivatives and 1,2,4-triazole-3-carboxylic acid ester derivatives, which are useful intermediates of the compound (VI-1), are desired.

First, the preparation of 2-acyl-5-benzylfuran derivatives is described below.

As a conventional route, for example, the following methods can be thought.

(Method X)

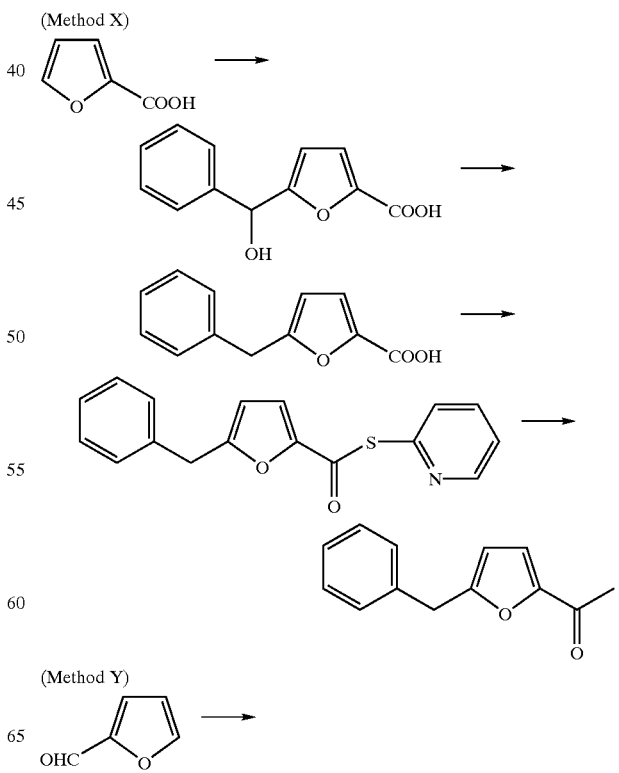

(Method Y)

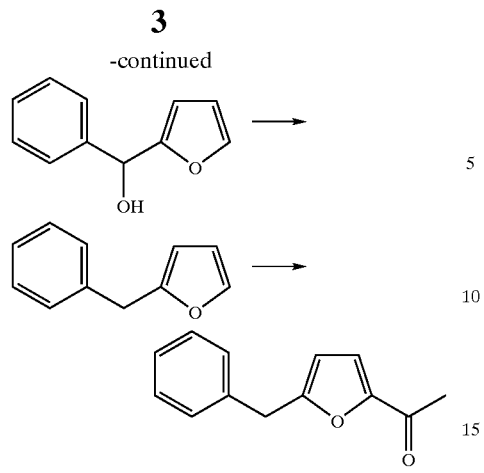

wherein any ring may be substituted with optionally substituted alkyl, optionally substituted alkoxy and/or halogen.

In method X, 2-furoic acid, a starting material is reacted with benzaldehyde. After removing the hydroxy group from the obtained compound, the carboxy group is esterified to give 2-pyridine thioester, which is reacted with methyl magnesium bromide to give 2-acetyl-5-benzylfuran. This method requires 2-pyridine thioester which is removed at the following step for converting the carboxy group to acetyl.

In method Y, furfural, a starting material, is reacted with phenyl magnesium bromide. After removing the hydroxy group of the obtained compound, 2-acetyl-5-benzylfuran is prepared through Friedel Crafts reaction. The final step of this method requires Friedel Crafts reaction which must be carried out under acidic condition. However, 2-benzylfuran is unstable under acidic condition, so 2-acyl-5-benzylfuran can not be prepared in high yield.

Since both of methods X and Y require many steps and many reagents, 2-acetyl-5-benzylfuran derivatives can not be industrially and commercially prepared.

The present inventors have solved the above problems on methods X and Y, and found out industrial and commercial processes for the preparation of 2-acyl-5-benzylfuran derivatives can be achieved through Friedel Crafts reaction of 2-acylfuran derivatives.

The present inventions of 2-acsyfuran derivatives include;

A-1) a process for the preparation of a compound of the formula (III-1):

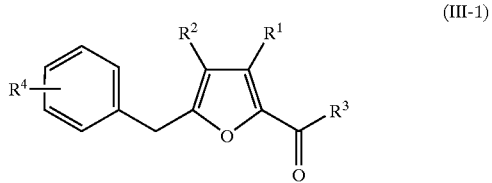

wherein $R^1$ and $R^2$ each is independently hydrogen, optionally substituted alkyl, optionally substituted alkoxy or halogen; $R^3$ is optionally substituted alkyl or optionally substituted alkoxy; and $R^4$ is hydrogen, optionally substituted alkyl, optionally substituted alkoxy or halogen, which comprises reacting a compound of the formula (I-1):

wherein $R^1$, $R^2$ and $R^3$ each is as defined above, with a compound of the formula (II-1):

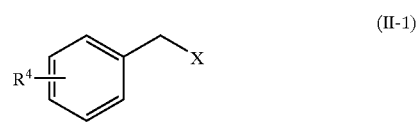

wherein $R^4$ is as defined above; and X is halogen, in the presence of a Lewis acid, A-2) the process according to the above A-1) wherein a reaction solvent is methylene chloride, A-3) the process according to the above A-1) wherein a reaction solvent is water, A-4) the process according to any one of the above A-1) to A-3) wherein $R^3$ is methyl, A-5) the process according to any one of the above A-1) to A-4) wherein $R^1$ and $R^2$ each is hydrogen, and A-6) the process according to any one of the above A-1) to A-5) wherein $R^4$ is 4-fluoro.

Second, the preparation of 1,2,4-triazole-3-carboxylic acid ester derivatives is described below.

A conventional process for the preparation of 1,2,4-triazole-3-carboxlic acid comprising a reduction of an isolated diazonium salt is accompanied with danger of explosion when a large amount of a diazonium salt is treated, so this process is not suitable to industrial production.

A process for the preparation of 1,2,4-triazole-3-carboxilic acid ester comprising a cyclization of acylamidrazone requires heating over a melting point, so this process is not suitable in an industrial scale, too.

Then, the present inventors have solved the above problems and found out processes for the preparation of 1,2,4-triazole-3-carboxilic acid ester derivatives as shown below, which are suitable in an industrial scale.

The present inventions of 1,2,4-triazole-3-carboxilic acid ester derivatives include;

B-1) a process for the preparation of a compound of the formula (IV-2):

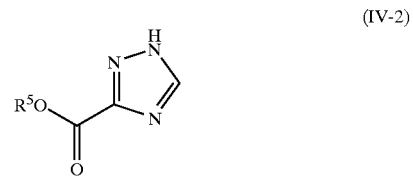

wherein $R^5$ is hydrogen or optionally substituted alkyl, which comprises reacting a compound of the formula (IV-1):

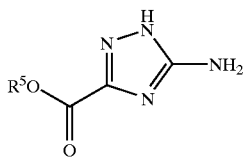

(IV-1)

wherein R⁵ is as defined above,
with an alkaline metal nitrite or an alkaline-earth metal nitrite in the presence of a reducing agent, B-2) the process according to the above B-1) which comprises reacting a compound of the formula (IV-1) with an alkaline metal nitrite in the presence of hypophosphorous acid as the reducing agent, B-3) the process according to the above B-1) or B-2) which is carried out under the addition of a small amount of alchol, B-4) the process according to any one of the above B-1) to B-3) wherein R⁵ is hydrogen, B-5) a process for the preparation of a compound of the formula (IV-3):

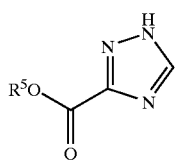

(IV-3)

wherein R⁵ is optionally substituted alkyl,
which comprises preparing 1,2,4-triazole-3-carboxilic acid through the process according to the above B-4) and esterifing the obtained compound, B-6) a process for a compound of the formula (IV-43):

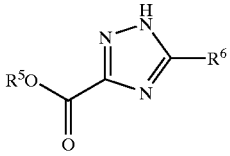

(IV-4)

wherein R⁵ is hydrogen or optionally substituted alkyl; and R⁶ is hydrogen,
optionally substituted alkyl or optionally substituted aryl, which comprises cyclizing a compound of the formula (V):

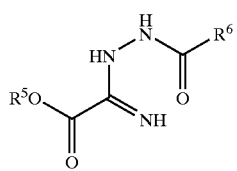

(V)

wherein R⁵ and R⁶ are as defined above,
in the presence of trialkylorthoester or a catalytic amount of an acid, B-7) the process according to the above B-6) wherein R⁵ is optionally substituted alkyl, B-8) the process according to the above B-6) wherein R⁵ is optionally substituted alkyl; and R⁶ is hydrogen, B-9) a process for the preparation of a compound of the formula (IV-6):

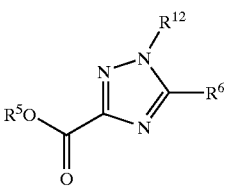

(IV-6)

wherein $R^5$ is optionally substituted alkyl; $R^6$ is hydrogen, optionally substituted alkyl or optionally substituted aryl; and $R^{12}$ is a group of the formula: —$R^7$ wherein $R^7$ is trityl, optionally substituted sulfamoyl or optionally substituted alkoxymethyl, a group of the formula: —$C(OR^8)R^9$—$CHR^{10}R^{11}$ wherein $R^8$ is optionally substituted alkyl; $R^9$, $R^{10}$ and $R^{11}$ each is independently hydrogen or optionally substituted alkyl; or $R^5$ and $R^{10}$ may be taken together to form optionally substituted alkylene, or hydroxymethyl, which comprises preparing a compound of the formula (IV-5):

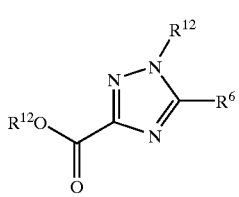

(IV-5)

wherein $R^5$ and $R^6$ are as defined above, through the process according to any one of the above B-1) to B-3) and B-5) to B-8), and reacting the obtained compound with a compound of the formula: $R^7X$ wherein $R^7$ is as defined above; and X is halogen, a compound of the formula: $(R^8O)R^9C=CR^{10}R^{11}$ wherein $R^8$, $R^9$, $R^{10}$ and $R^{11}$ are as defined above, or formaldehyde, B-10) a process of the preparation of a compound of the formula (IV-8):

(IV-8)

wherein $R^6$ is hydrogen, optionally substituted alkyl or optionally substituted aryl; and $R^{12}$ is a group of the formula: —$R^7$ wherein $R^7$ is trityl, optionally substituted sulfamoyl or optionally substituted alkoxymethyl, a group of the formula: —$C(OR^8)R^9$—$CHR^{10}R^{11}$ wherein $R^8$ is optionally substituted alkyl; $R^9$, $R^{10}$ and $R^{11}$ each is independently hydrogen or optionally substituted alkyl, or $R^8$ and $R^{10}$ may be taken together to form optionally substituted alkylene, or hydroxymethyl, which comprises preparing a compound of the formula:(IV-7):

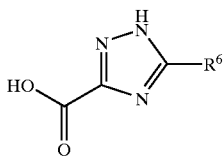

(IV-7)

wherein $R^6$ is as defined above, through the process according to the above B-4) or B-6), and reacting the obtained compound with a compound of the formula: $R^7X$ wherein $R^7$ is as defined above; and X is halogen, a compound of the formula: $(R^8O)R^9C=CR^{10}R^{11}$ wherein $R^8$, $R^9$, $R^{10}$ and $R^{11}$ are as defined above, or formaldehyde, B-11) the process according to the above B-9) or B-10) which comprises reacting a compound of the formula (IV-7) with a compound of the formula: $R^7X$ wherein $R^7$ is trityl, B-12) the process according to the above B-9) or B-10) which comprises reacting a compound of the formula (IV-7) with a compound of the formula: $(R^8O)R^9C=CR^{10}R^{11}$ wherein $R^5$ and $R^{10}$ are taken together to form trimethylene; and $R^9$ and $R^{11}$ a hihydrogen, B-13) the process according to the above B-9) or B-10) which comprises reacting a compound of the formula (IV-7) with a compound of the formula: $(R^8O)R^9C=CR^{10}R^{11}$ wherein $R^8$ and $R^9$ each is methyl; and $R^{10}$ and $R^{11}$ each is hydrogen, B-14) a compound of the formula (IV-9):

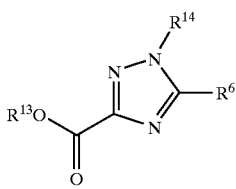

(IV-9)

wherein $R^6$ is hydrogen or alkyl; $R^{13}$ is alkyl, a group of the formula: —$R^7$ wherein $R^7$ is trityl, optionally substituted sulfamoyl or alkoxymethyl, a group of the formula: —$C(OR^8)R^9$—$CHR^{10}R^{11}$ wherein $R^8$ is alkyl; $R^9$, $R^{10}$ and $R^{11}$ each is independently hydrogen or alkyl; or $R^8$ and $R^{10}$ may be taken together to form alkylene, or hydroxymethyl; and $R^{14}$ is a group of the formula: —$R^7$ wherein $R^7$ is as defined above, a group of the formula: —$C(OR^8)R^9$—$CHR^{10}R^{11}$ wherein $R^8$, $R^9$, $R^{10}$ and $R^{11}$ are defined above, or hydroxymethyl, provided that a compound wherein $R^6$ is hydrogen; $R^{13}$ is methyl; and $R^{14}$ is trityl, a compound wherein $R^6$ is hydrogen; $R^{13}$ is methyl; and $R^{14}$ is tetrahydropyran-2-yl, and a compound wherein $R^6$ is hydrogen; $R^{13}$ is ethyl; and $R^{14}$ is trityl are excluded, B-15) the compound according to the above B-14) wherein $R^6$ is hydrogen;

$R^{13}$ is methyl or ethyl; and $R^{14}$ is tetrahydropyran-2-yl, hydroxymethyl, methoxymethyl, ethoxymethyl, N,N-dimethylsulfamoyl, (1-methoxy-1-methyl)ethyl, (1-ethoxy)ethyl, (1ethoxy-1-methyl)ethyl, (1-n-propoxy)ethyl, (1-n-butoxy)ethyl or (1-isobutoxy)ethyl.

The present inventions for the preparation of substituted propenone derivatives accompanied by the above A) and/or B) include;

C-1) a process for the preparation of a compound of the formula (VI-1):

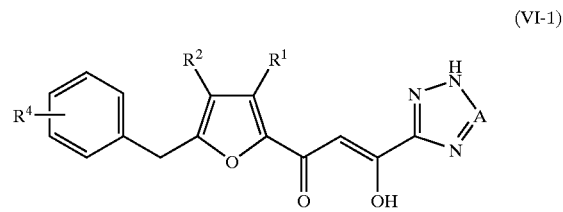

(VI-1)

wherein $R^1$, $R^2$ and $R^4$ each is independently hydrogen, optionally substituted alkyl, optionally substituted alkoxy or halogen; A is $CR^6$ or NA; and $R^6$ is hydrogen, optionally substituted alkyl or optionally substituted aryl, which comprises preparing a compound of the formula (III-2):

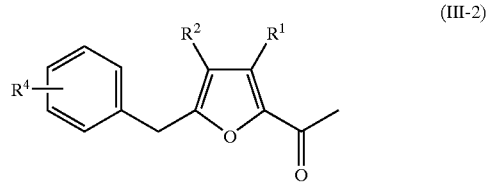

(III-2)

wherein $R^1$, $R^2$ and $R^4$ are as defined above, through the process according to the above A-4), reacting the compound of the formula (III-2) with a compound of the formula (IV-10):

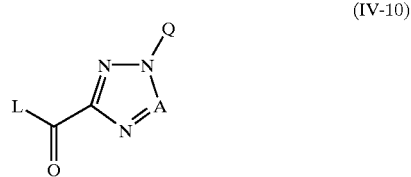

(IV-10)

wherein A is as defined above, Q is a protecting group; and L is a leaving group, in the presence of a base, and deprotecting Q, C-2) the process according to the above C-1) wherein $R^1$ and $R^2$ each is hydrogen; and $R^4$ is halogen, C-3) the process according to the above C-1) or C-2) wherein $R^4$ is 4-fluoro, C-4) the process according to any one of the above C-1) to C-3) wherein A is CH, C-5) a process for the preparation of a compound of the formula (IV-2):

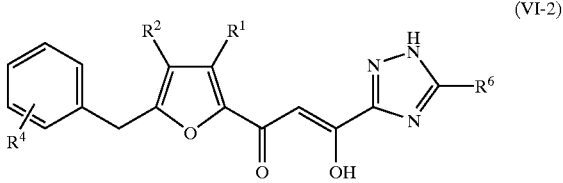

(VI-2)

wherein $R^1$, $R^2$ and $R^4$ each is independently hydrogen, optionally substituted, alkyl, optionally substituted alkoxy or halogen; and $R^6$ is hydrogen, optionally substituted alkyl or optionally substituted aryl, which comprises preparing a compound of the formula (IV-11):

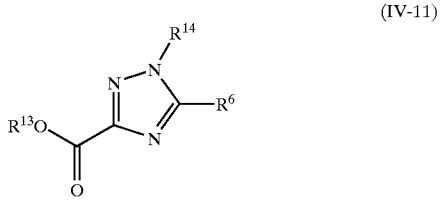

(IV-11)

wherein R⁶ is as defined above, R¹³ is optionally substituted alkyl, a group of the formula: —R⁷ wherein R⁷ is trityl, optionally substituted sulfamoyl or, optionally substituted alkoxymethyl, a group of the formula: —C(OR⁸)R⁹—CHR¹⁰R¹¹ wherein R⁸ is alkyl; R⁹, R¹⁰ and R¹¹ each is independently hydrogen or optionally substituted alkyl; or R⁸ and R¹⁰ may be taken together to form alkylene, or hydroxymethyl; and R¹⁴ is a group of the formula: —R⁷ wherein R⁷ is as defined above, a group of the formula: —C(OR⁸)R⁹—CHR¹⁰R¹¹ wherein R⁸, R⁹, R¹⁰ and R¹¹ are defined above, or hydroxymethyl, through the process according to the above B-9) or B-10), reacting the obtained compound with a compound of the formula (III-2):

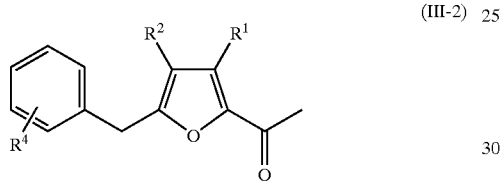

(III-2)

wherein R¹, R² and R⁴ are as defined above, and deprotecting R¹⁴,

C-6) the process according to the above C-5) which comprises preparing the compound of the formula (III-2):

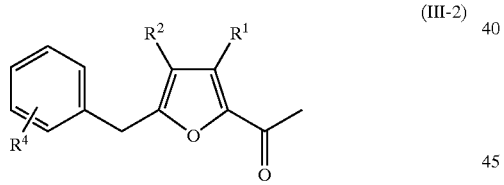

(III-2)

wherein R¹, R² and R⁴ each is independently hydrogen, optionally substituted alkyl, optionally substituted alkoxy or halogen through the process according to the above A-4), C-7) the process according to the above C-5) or C-6) wherein R¹, R² and R⁶ each is hydrogen; and R⁴ is halogen, C-8) a compound of the formula (VI-7):

(VI-7)

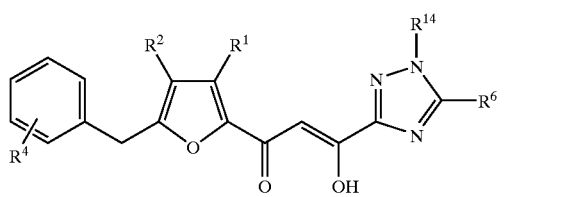

wherein R¹, R² and R⁴ each is independently hydrogen, optionally substituted alkyl, optionally substituted alkoxy or halogen; R⁶ is hydrogen, optionally, substituted alkyl or optionally substituted aryl; and R¹⁴ is a group of the formula: —R⁷ wherein R⁷ is trityl, optionally substituted sulfamoyl or optionally substituted alkoxymethyl, a group of the formula: —C(OR⁸)R⁹—CHR¹⁰R¹¹ wherein R⁸ is alkyl; R⁹, R¹⁰ and R¹¹ each is independently hydrogen or optionally substituted alkyl; or R⁸ and R¹⁰ may be taken together to form alkylene, or hydroxymethyl, and C-9) the compound according to the above C-8) wherein R⁴ is 4-fluoro; R¹, R² and R⁶ each is hydrogen; and R¹⁴ is trityl, tetrahydropyran-2-yl, hydroxymethyl, methoxymethyl, ethoxymethyl, N,N-dimethylsulfamoyl, (1-methoxy-1-methyl)ethyl, (1-ethoxy)ethyl, (1-ethoxy-1-methyl)ethyl, (1-n-propoxy)ethyl, (1-n-butoxy)ethyl or (1-isobutoxy)ethyl.

The present inventions for a crystal of the above novel substituted propenone derivative include;

D-1) a crystal of an isomer having a chemical structure of the formula (VI-1):

(VI-1)

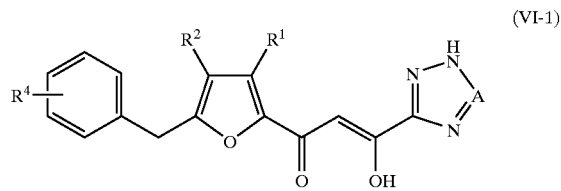

wherein A is CR⁶ or N; R⁶ is hydrogen, optionally substituted alkyl or optionally substituted aryl; and R¹, R² and R⁴ each is independently hydrogen, optionally substituted alkyl, optionally substituted alkoxy or halogen, D-2) the crystal according to the above D-1) wherein R¹ and R² each is hydrogen; R⁴ is p-fluoro; and A is CH, D-3) the crystal according to the above D-2) of which crystal parameters by single crystal X-ray diffraction are unit cell constants a=32.432(2) Å, b=10.886(2) Å, c=7.960(2) Å, α=90.00°, β=90.00°, γ=90.00°, V=2810 (1) Å³, Z=8; a space group Pbca; and density of 1.481 g/cm³, D-4) the crystal according to the above D-2) of which diffraction angles (2θ) of main peaks by powder X-ray diffraction are 20.380, 21.280, 21.340, 23.140, 23.360, 23.540, 25.860, 27.460, 27.500, 28.100, 28.180, 29.400 and 29.480 (degree), D-5) a crystal of an isomer having a chemical structure of the formula (VI-4):

(VI-4)

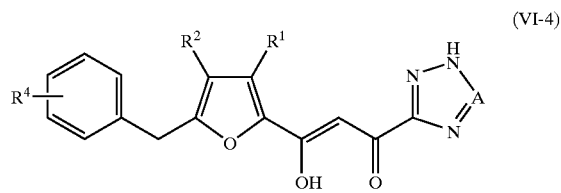

wherein A is CR⁶ or N; R⁸ is hydrogen, optionally substituted alkyl or optionally substituted aryl; and R¹, R² and R⁴ each is independently hydrogen, optionally substituted alkyl, optionally substituted alkoxy or halogen, D-6) the crystal according to the above D-5) wherein R¹ and R² each is hydrogen; R⁴ is p-fluoro; and A is CH, D-7) the crystal according to the above D-6) of which crystal parameters by single crystal X-ray diffraction are unit cell constants a=11.9003(7) Å, b=9.7183(5) Å, c=13.2617(8) Å, α=90.00°, β=109.450(4)°, γ=90.00°, V=1446.2(1) Å³ and Z=4; a space group P2₁/n; and density of 1.439 g/cm³, D-8) the crystal according to the above D-6) of which diffraction angles (2θ) of main peaks by powder X-ray diffraction are 8.760, 19.600, 22.080, 23.760, 26.200, 27.580 and 29.080 (degree), and D-9) a crystal of an isomer of 1-[5-(4-fluorobenzyl)furan-2-yl]-3-hydroxy-3-(1H-1,2,4-triazole-3-yl)propenone of which diffraction angles (2θ) of main peaks by powder X-ray diffraction are 10.520, 13.860, 15.680, 18.160, 22.840, 26.180 and 28.120 (degree).

Each term to be used in the present specification is explained below.

The term "alkyl" includes C1 to C6 straight or branched alkyl, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl or the like. Preferred is methyl or ethyl.

The term "alkylene" includes C2 to C6 straight or branched alkylene, for example, ethylene, propylene, trimethylene, ethylethylene, tetramethylene or the like. Preferred is trimethylene.

The term "alkoxy" includes C1 to C6 straight or branched alkoxy, for example, methoxy, ethoxy, n-propoxy, isopropoxy, n-butoxy, isobutoxy, sec-butoxy, tert-butoxy, n-pentyloxy, isopentyloxy, neopentyloxy, tert-pentyloxy, n-hexyloxy, isohexyloxy or the like. Preferred is methoxy or ethoxy.

The term "alkoxymethyl" includes methyl group substituted with the above alkyloxy, for example, methoxymethyl, ethoxymethyl, n-propoxymethyl, isopropoxymethyl, n-butoxymethyl, isobutoxymethyl, sec-butoxymethyl, tert-butoxymethyl, n-pentyloxymethyl, isopentyloxymethyl, neopentyloxymethyl, tert-pentyloxymethyl, n-hexyloxymethyl, isohexyloxymethyl or the like. Preferred is methoxy or ethoxymethyl.

The term "aryl" includes C6 to C14 aromatic carbocycle, for example, phenyl, naphthyl, anthryl, phenanthryl or the like. Preferred is phenyl.

The term "halogen" includes fluoro, chloro, bromo or iodo. Preferred in X is chloro or bromo. Preferred in R¹³ is fluoro, especially para-substituted fluoro.

The term "trityl" means a group of the formula: —CPh₃ wherein Ph is phenyl.

The term "optionally substituted sulfamoyl" includes unsubstituted sulfamoyl and sulfamoyl mono- or di-substituted with alkyl, for, example, sulfamoyl, N-methylsulfamoyl, N,N-dimethylsulfamoyl, N-ethylsulfamoyl, N,N-diethylsulfamoyl or the like.

The substituents of "optionally substituted alkyl", "optionally substituted alkoxymethyl" and "optionally substituted alkylene" include aryl. (e.g., phenyl or the like), cycloalkyl (e.g., cyclopropyl, cyclopentyl, cyclohexyl or the like), cyano, nitro, hydroxy, amino, halogenated alkyl (e.g., trifluoromethyl or the like) or the like.

The substituents of "optionally substituted aryl" include alkyl (e.g, methyl, ethyl or the like), alkenyl (e.g., vinyl, allyl or the like), halogen, hydroxy, alkoxy (e.g., methoxy, ethoxy or the like), halogenated alkyl (e.g., trifluoromethyl or the like), nitro, sulfamoyl, amino, alkyl-substituted amino (e.g., methylamino, dimethylamino or the like), carboxy, alkoxycarbonyl (e.g., methoxycarbonyl or the like), cyano or the like.

BEST MODE FOR CARRYING OUT THE INVENTION

Figure 1:
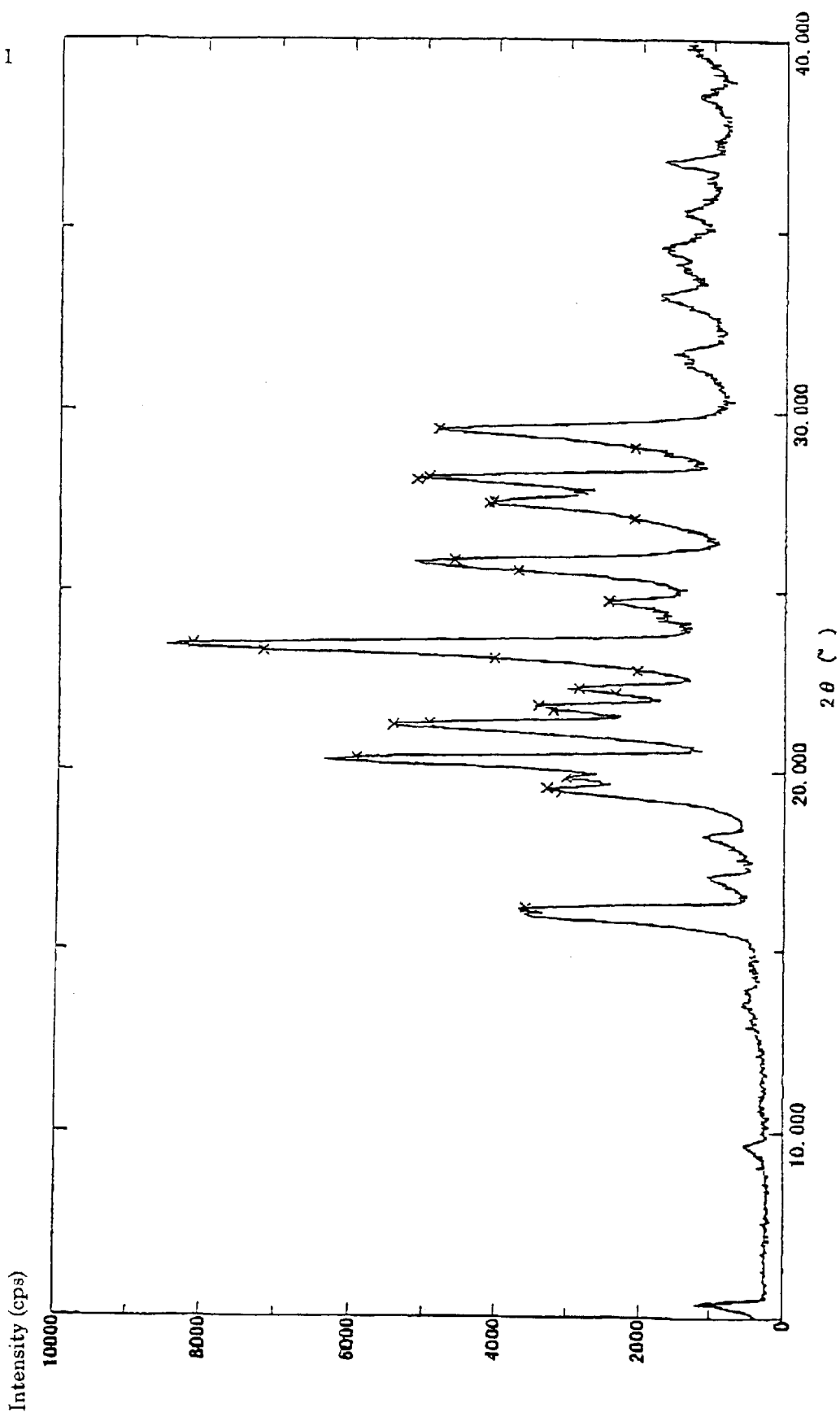
FIG. 1 shows a powder X-ray diffraction chart of a crystal (type I) of 1-[5-(4-fluorobenzyl)furan-2-yl]-3-hydroxy-3-(1H-1,2,4-triazole-3-yl)propenone.
Figure 2:
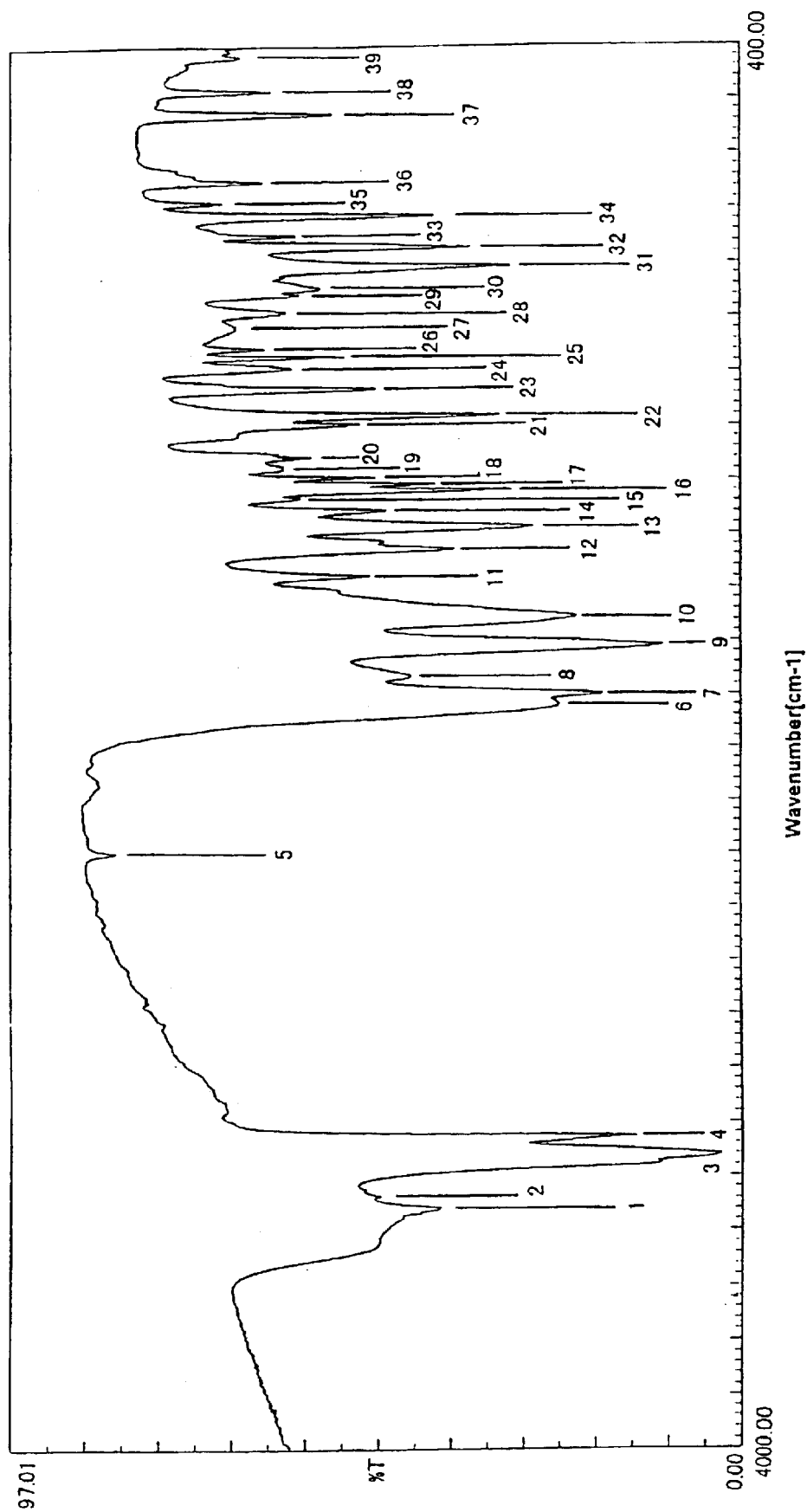
FIG. 2 shows an infrared absorption spectrum chart of a crystal (type I) of 1-[5-(4-fluorobenzyl)furan-2-yl]-3-hydroxy-3-(1H-1,2,4-triazole-3-yl)propenone.
Figure 3:
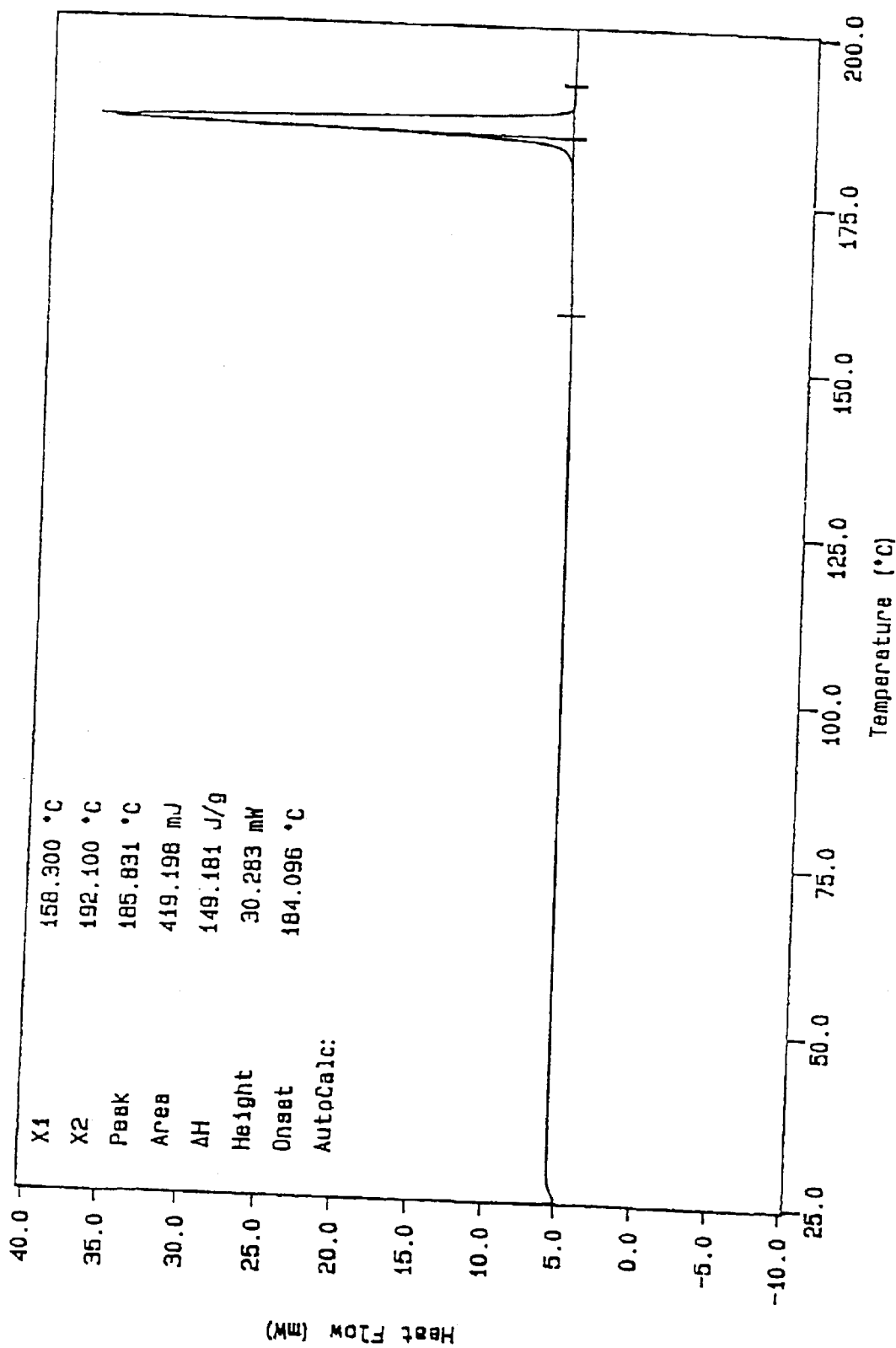
FIG. 3 shows a diffrential scanning calorimetry chart of a crystal (type I) of 1-[5-(4-fluorobenzyl)furan-2-yl]-3-hydroxy-3-(1H-1,2,4-triazole-3-yl)propenone.
Figure 4:
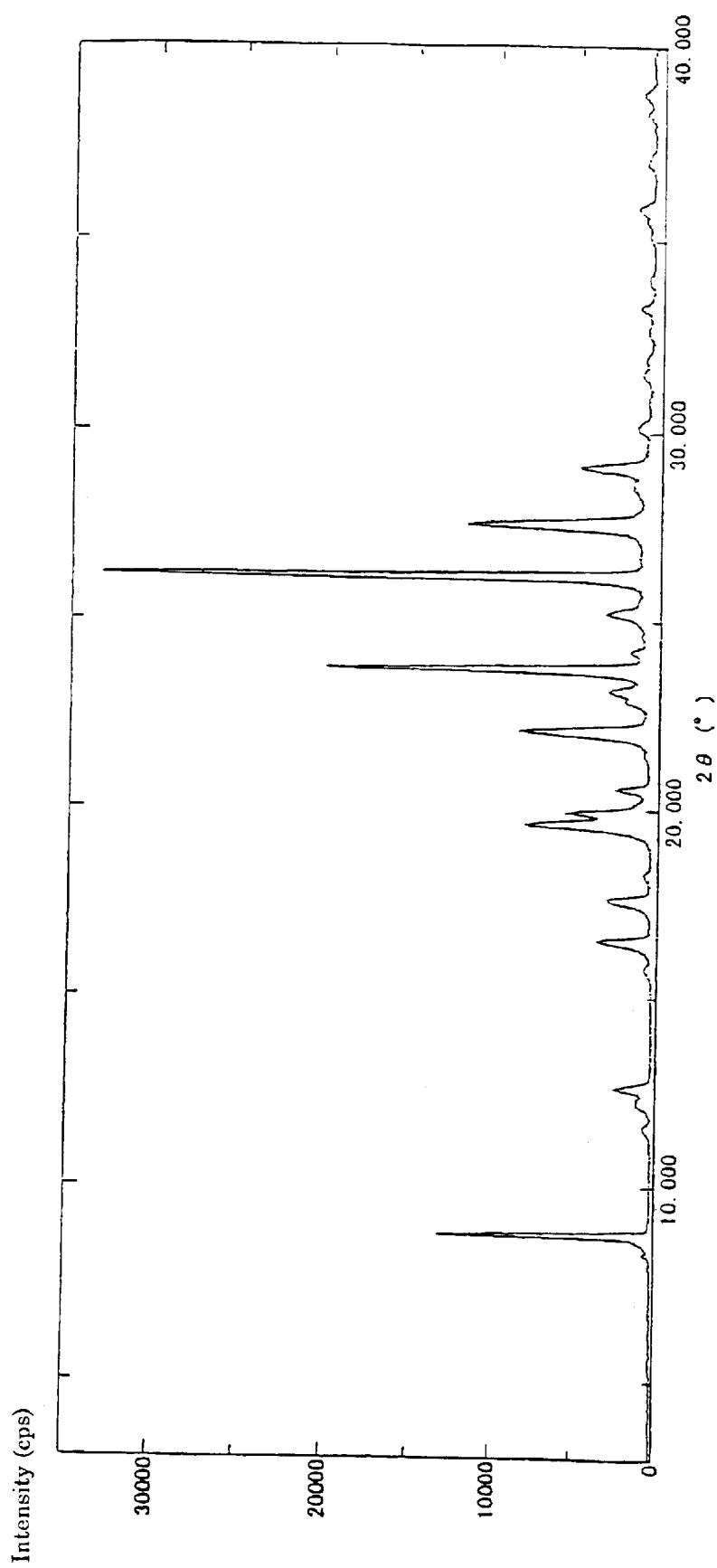
FIG. 4 shows a powder X-ray diffraction chart of a crystal (type II) of 1-[5-(4-fluorobenzyl)furan-2-yl]-3-hydroxy-3-(1H-1,2,4-triazole-3-yl)propenone.
Figure 5:
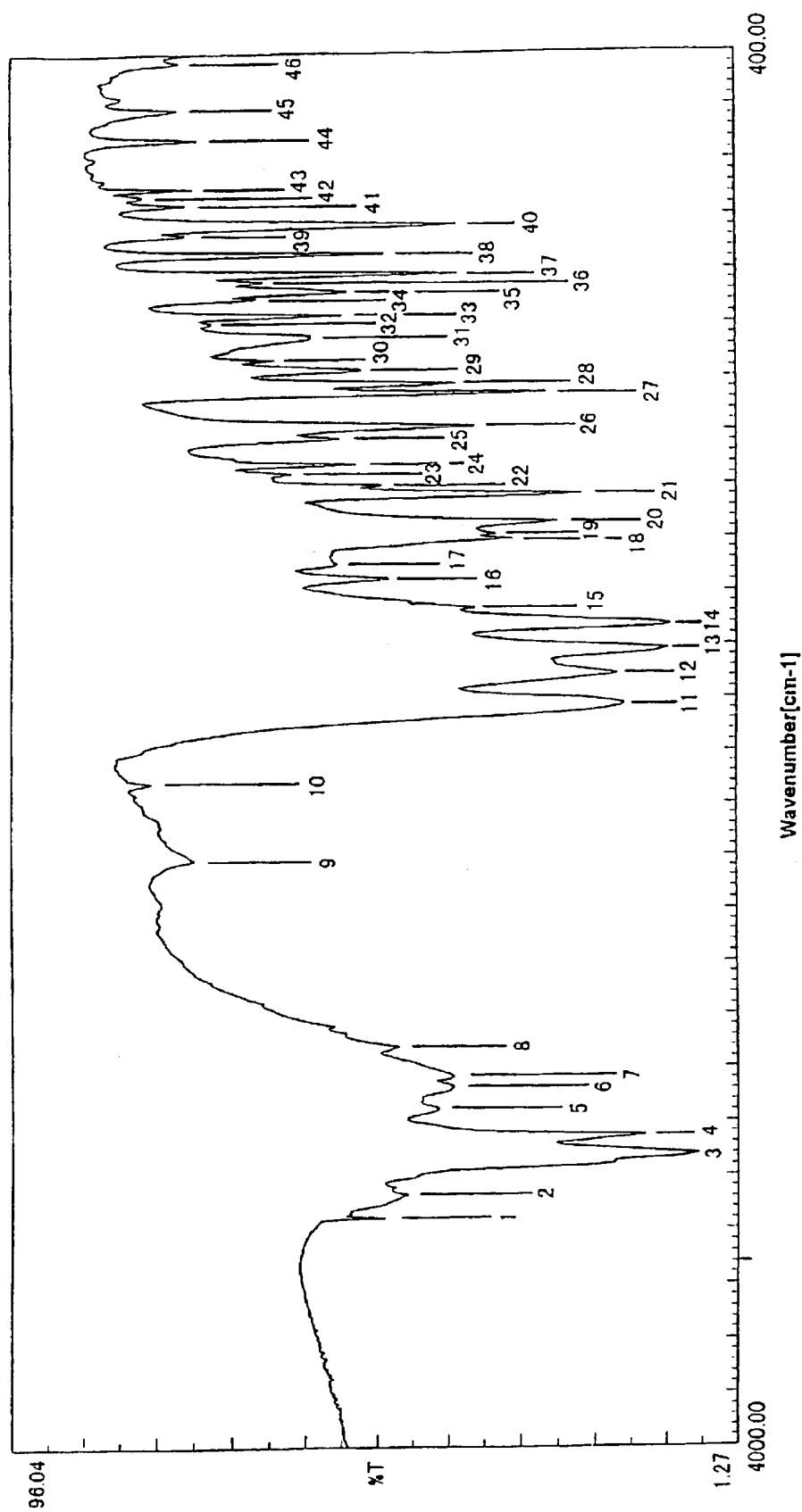
FIG. 5 shows an infrared absorption spectrum chart of a crystal (type II) of 1-[5-(4-fluorobenzyl)furan-2-yl]-3-hydroxy-3-(1H-1,2,4-triazole-3-yl)propenone.
Figure 6:
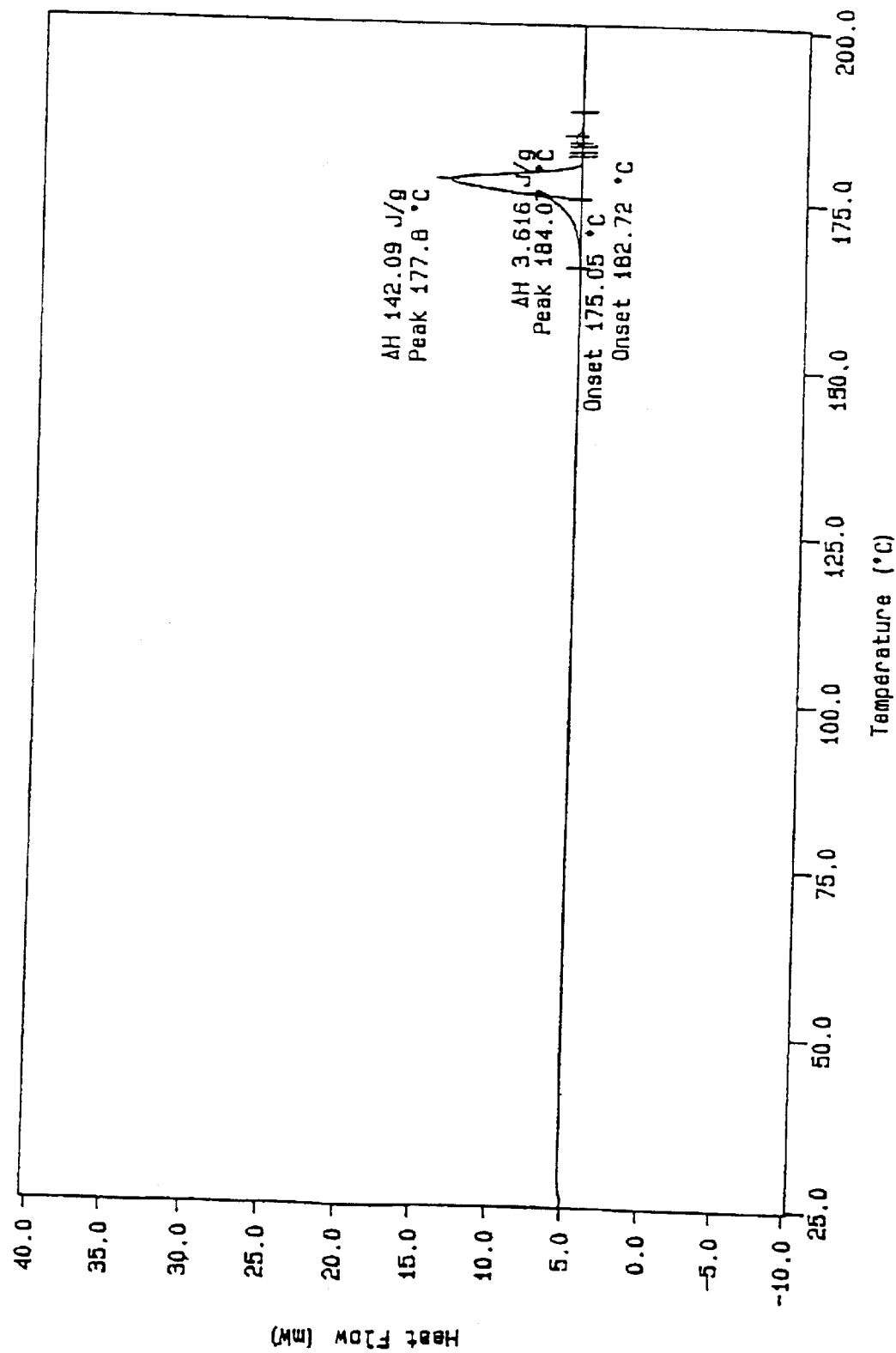
FIG. 6 shows a diffrential scanning calorimetry chart of a crystal (type II) of 1-[5-(4-fluorobenzyl)furan-2-yl]-3-hydroxy-3-(1H-1,2,4-triazole-3-yl)propenone.
Figure 7:
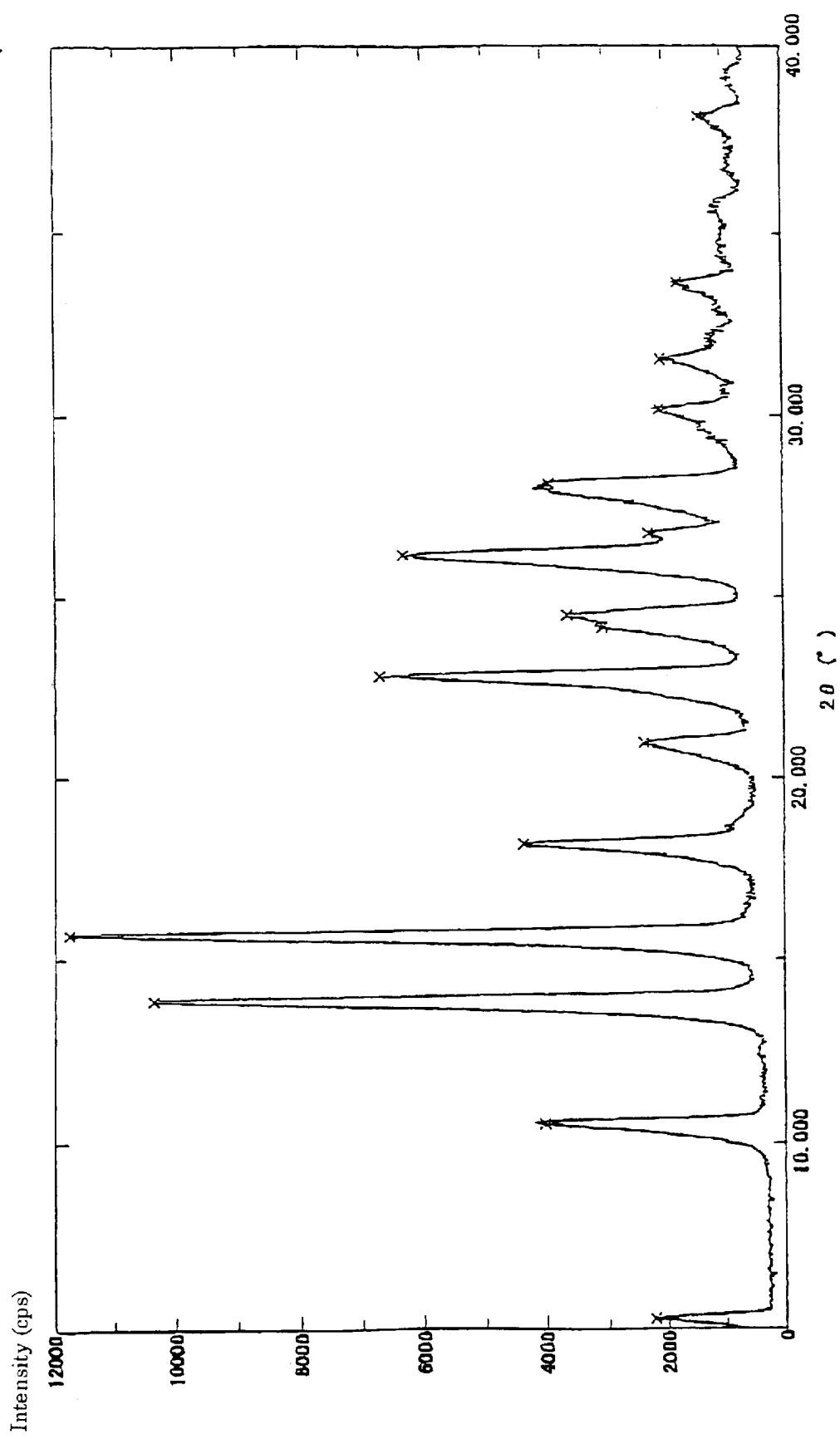
FIG. 7 shows a powder X-ray diffraction chart of a crystal (type III) of 1-[5-(4-fluorobenzyl)furan-2-yl]-3-hydroxy-3-(1H-1,2,4-triazole-3-yl)propenone.
Figure 8:
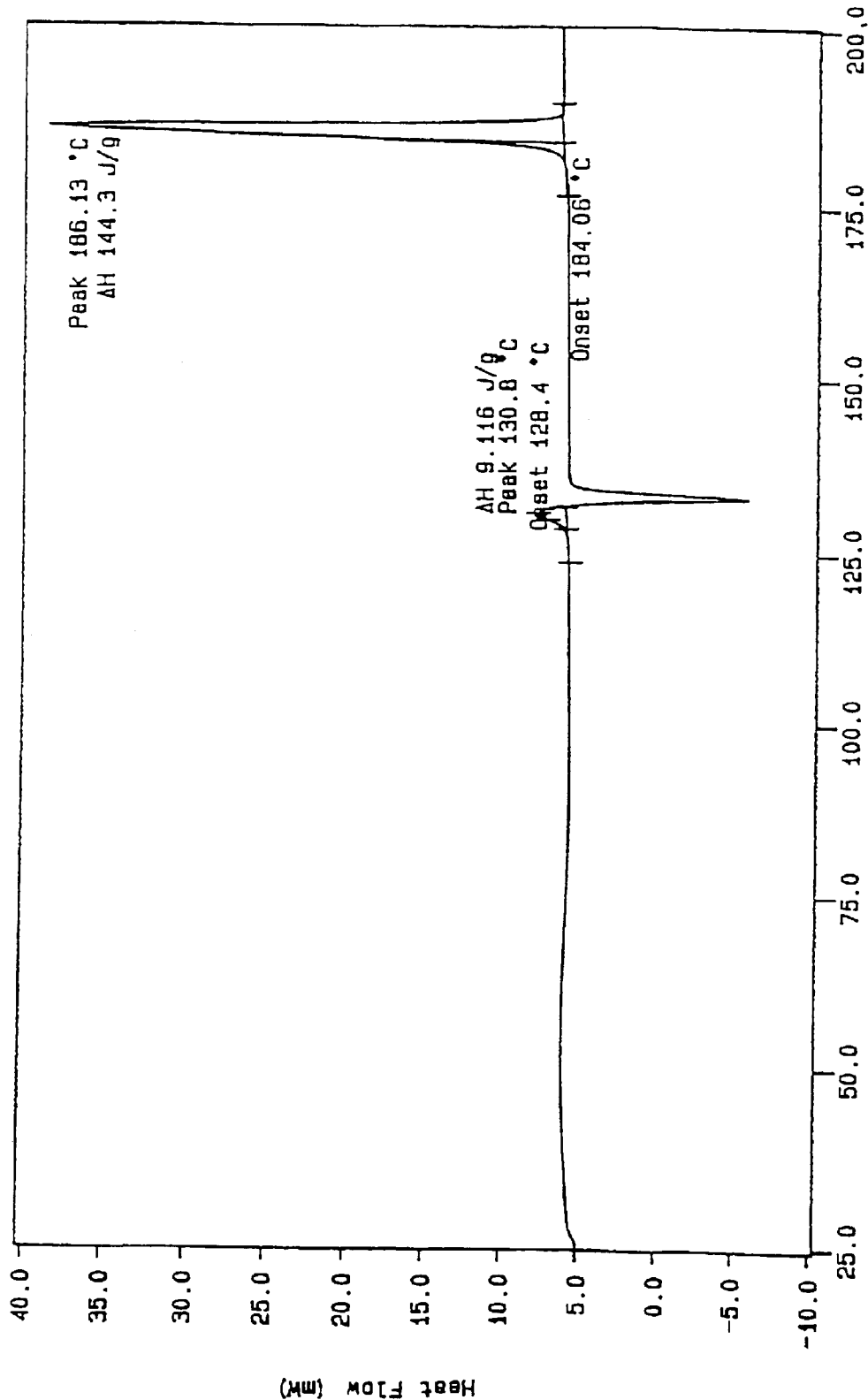
FIG. 8 shows an infrared absorption spectrum chart of a crystal (type III) of 1-[5-(4-fluorobenzyl)furan-2-yl]-3-hydroxy-3-(1H-1,2,4-triazole-3-yl)propenone.
Figure 9:
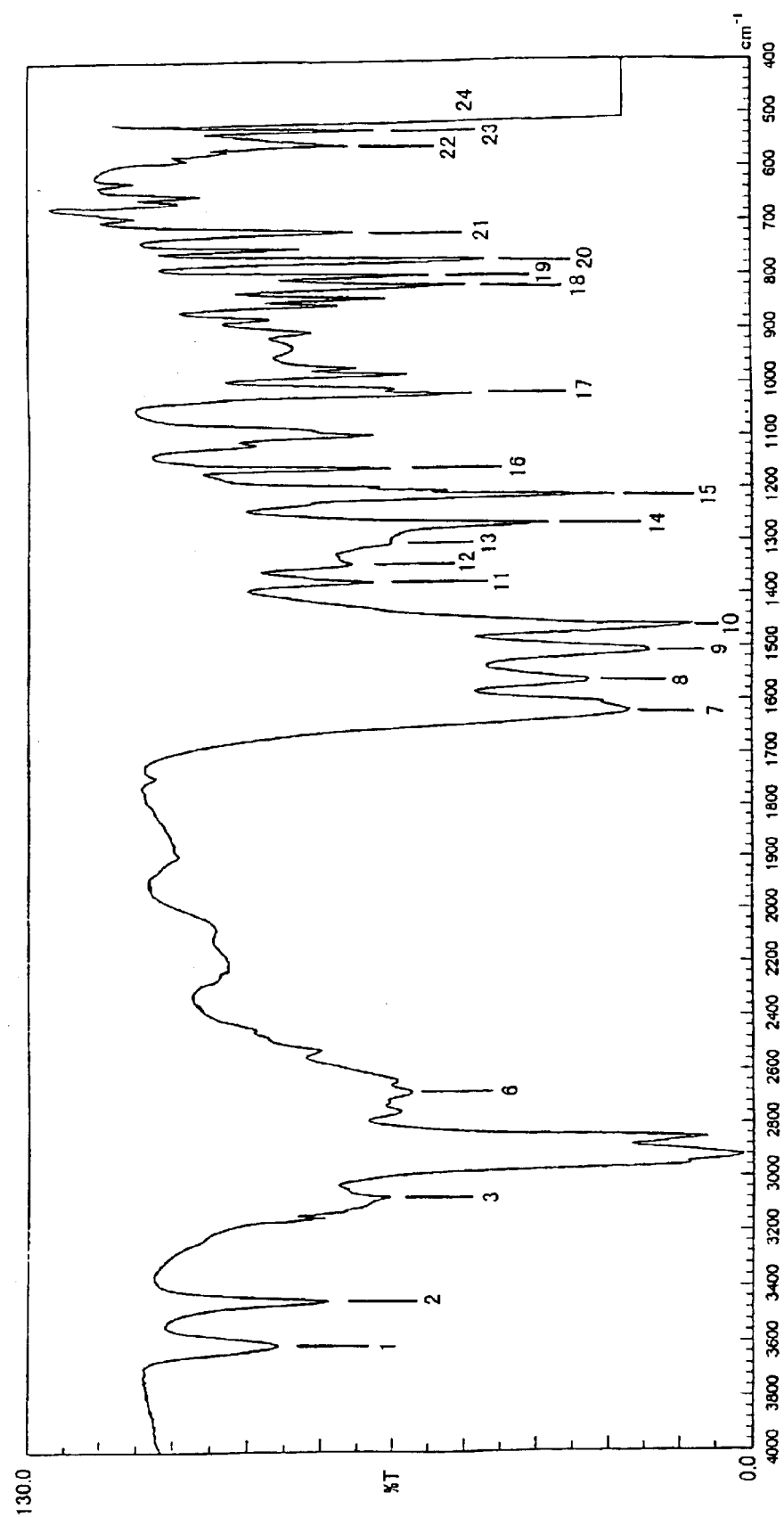
FIG. 9 shows a diffrential scanning calorimetry chart of a crystal (type III) of 1-[5-(4-fluorobenzyl)furan-2-yl]-3-hydroxy-3-(1H-1,2,4-triazole-3-yl)propenone.

The present inventions are explained with the following process A, process B and process C.

First, a process for the preparation of 2-acyl-5-benzylfuran derivatives is explained below.

Process A1

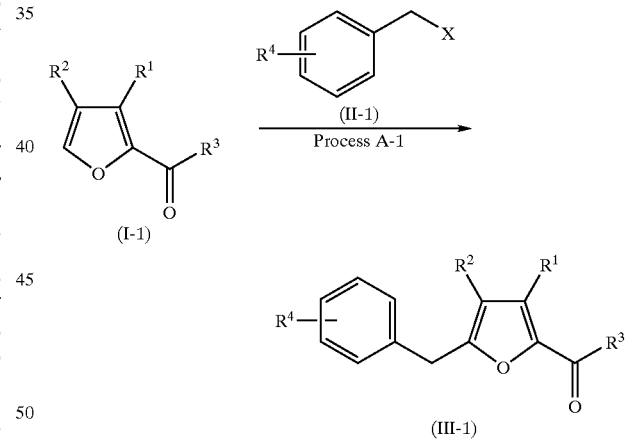

wherein R¹, R² and R⁴ each is independently hydrogen, optionally substituted alkyl, optionally substituted alkoxy or halogen; R³ is optionally substituted alkyl or optionally substituted alkoxy.

This scheme shows a process for the preparation of 2-acyl-5-benzylfuran derivatives (III-1) which comprises reacting 2-acylfuran derivatives (I-1) with benzylhalide derivatives (II-1) in the presence of a Lewis acid through Friedel Crafts reaction.

The compound (I-1) includes 2-acetylfuran, 2-acetyl-3-methylfuran, 2-acetyl-4-methylfuran, 2-acetyl-3,4-dimethylfuran, 2-acetyl-3-methoxyfuran, 2-acetyl-4-methoxyfuran, 2-acetyl-3,4-dimethoxyfuran, 2-acetyl-3-chlorofuran, 2-acetyl-4-chlorofuran, 2-acetyl-3,4-dichlorofuran, 2-propionylfuran, 3-methyl-2- propionylfuran, 4-methyl-2-propionylfuran, 3,4-dimethyl-2-propionylfuran, 3-methoxy-2-propionylfuran, 4-methoxy-2-propionylfuran, 3,4-dimethoxy-2-propionylfuran, 3-chloro-2-propionylfuran, 4-chloro-2-propionylfuran, 3,4-dichloro-2-propionylfuran, methyl 2-furoic acetate, ethyl 2-furoic acetate or the like. Preferred is 2-acetylfuran.

The compound (II-1) includes benzylchloride, benzylbromide, 4-methylbenzylchloride, 4-methylbenzylbromide, 4-methoxybenzylchloride, 4-methoxybenzylbromide, 4-fluorobenzylchloride, 4-fluorobenzylbromide, 4-chlorobenzylchloride, 4-chlorobenzylbromide, 3-methylbenzylchloride, 3-methylbenzylbromide, 3-methoxybenzylchloride, 3-methoxybenzylbromide, 3-fluorobenzylchloride, 3-fluorobenzylbromide, 3-chlorobenzylchloride, 3-chlorobenzylbromide or the like. Preferred is 4-fluorobenzylchloride or 4-fluorobenzylbromide.

A Lewis acid includes zinc chloride ($ZnCl_2$), stannic chloride ($SnCl_4$), ferric chloride (III) ($FeCl_3$), aluminum chloride ($AlCl_3$), $BF_3$/ether or the like. Preferred is zinc chloride or stannic chloride.

This process can be performed without a reaction solvent. When a reaction solvent is used, water, carbon disulfide, methylene chloride, dichloroethane, chloroform or the like can be used. Preferred is water or methylene chloride.

When methylene chloride is used as a reaction solvent, the produced compound (III-1) forms a complex with a Lewis acid, a crystal of which is precipitated in the reaction solvent. The crystal is filtered off, dissolved in water, extracted with an organic solvent to give the compound (III-1) in high quality.

When water is used as a reaction solvent, the reaction can be performed mildly, which is economically and environmentally preferable.

The reaction temperature is −50 to 150° C., preferably, 0 to 100° C.

The reaction time is 1 to 48 hours, preferably 1 to 24 hours.

2-Acyl-5-benzylfuran derivatives such as a compound (III-1) or (III-2) can be prepared through the following processes such as Process A-2 and A-3 besides the above Process A1.

Process A2

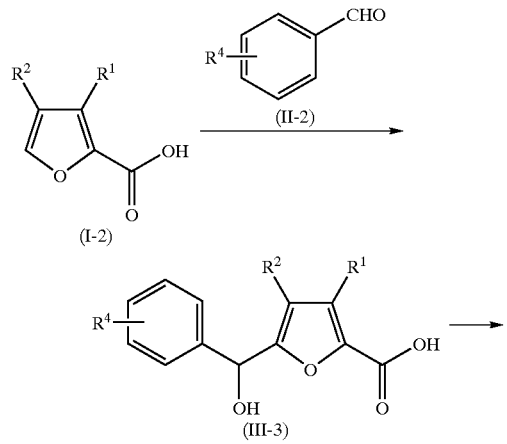

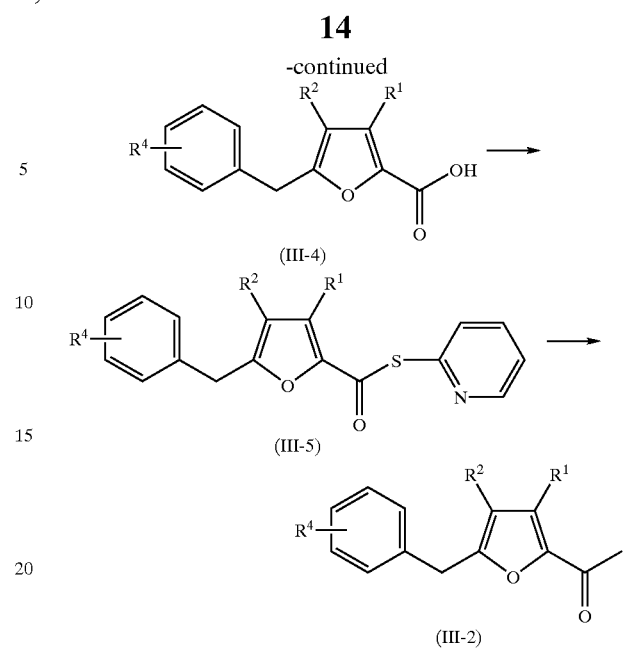

wherein $R^1$, $R^2$ and $R^4$ each is independently hydrogen, optionally substituted alkyl, optionally substituted alkoxy or halogen.

The above process includes the following four steps. First, a coupling reaction of a compound (I-2) and (II-2) produces a compound (III-3). Second, a dehydroxy reaction of the compound (III-3) produces a compound (III-4). Third, an introduction of a leaving group to a carboxy group of the compound (III-4) produces a compound (III-5). Finally, a reaction of the compound (III-5) with methyl magnesium halide (e.g., methyl magnesium bromide) produces a compound (III-2).

The above coupling reaction can be performed in the presence of a base (e.g., LDA) under cooling.

The dehydroxy reaction can be preformed by reduction with trimethyl chlorosilane and sodium iodide. This reaction can be performed by a hydrogenation in the presence of palladium carbon after an acetylation with acetic anhydride in the presence of triethylamine.

The converting of a carboxy group to an acetyl group can be performed by the following steps. First, a compound (III-4) is reacted with thionylhalide (e.g., thionylchloride) in the presence of a catalytic amount of dimethylformamide or the like. Second, the obtained compound is reacted with methyl magnesium halide (e.g., methyl magnesium chloride) in the presence of a catalytic amount of ironic acetyl acetonate.

Process A3

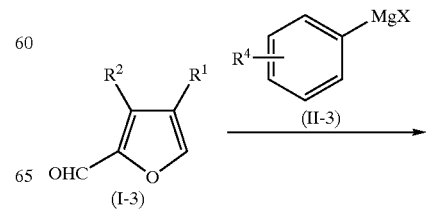

-continued

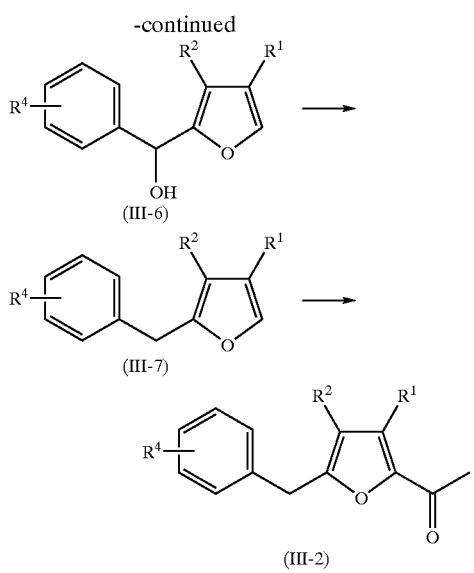

wherein $R^1$, $R^2$ and $R^4$ each is independently hydrogen, optionally substituted alkyl, optionally substituted alkoxy or halogen; and X is halogen.

The above process for the preparation of a compound (III-2) comprises reacting a compound (I-3), a starting material, with a compound (II-3), removing a hydroxy group, and Friedel-Crafts reaction.

Second, the process for the preparation of 1,2,4-triazole-3-carboxylic acid ester derivatives is explained below.

Process B1

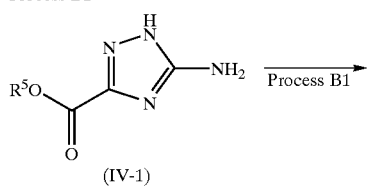

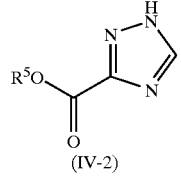

wherein $R^5$ is hydrogen or optionally substituted alkyl.

This scheme shows a process for the preparation of a compound (IV-2) which includes a deamination of a compound (IV-1), in detail, a directly deamination without isolating a diazonium salt.

An alkali metal nitrite to-be used includes sodium nitrite, potassium nitrite, lithium nitrite or the like. Preferred is sodium nitrite.

An alkaline-earth metal nitrite can be used in place of alkali metal nitrite. An alkaline-earth metal nitrite includes calcium nitrite or the like.

A reducing agent includes hypophosphorous acid ($H_3PO_2$), phosphorous acid ($H_3PO_3$), $Ca(H_2PO_2)_2$, NaBH(OAc)$_3$, PhSH, $H_2CO$ or the like. Preferred is hypophosphorous acid ($H_3PO_2$).

To a compound (IV-1) is added an aqueous solution of a reducing agent (e.g., hypophosphorous acid) and warmed at 30 to 60° C. (preferably, 40 to 50° C.). To the suspension is added dropwise under stirring at 30 to 60° C. (preferably, under 50° C.) for approximately 10 to 60 minutes (preferably approximately 30 minutes) an aqueous solution of an alkali metal nitrite or an alkaline-earth metal nitrite. After addition, the reaction mixture is stirred at the same temperature for 10 to 60 minutes (preferably 30 minutes), cooled to 0–20° C. (preferably, approximately 5° C.) and stirred for 10 to 60 minutes (preferably, approximately 30 minutes). The objective, a compound (IV-2) can be prepared by filtering the obtained suspension.

This process may be performed in the presence of a diluted hydrochloric acid (e.g., 6% hydrochloric acid) or the like.

Preferred in this process is an addition of a small amount (1–10 (v/v) %, preferably, 2–3 (v/v) % to all volume of a solvent to be used, or approximately 0.2 mole equivalent to a compound (I)) of alcohol. A gas is produced for approximately 10 minutes by adding an aqueous solution of an alkali metal nitrite. An addition of alcohol suppresses a vigorous production of the gas as well as controlling the adding rate of an aqueous solution of an alkali metal nitrite.

An alcohol includes an alkyl alcohol, for example, isopropylalcohol, isobutanol, methanol, ethanol, n-propylalcohol, n-butanol or the like. Preferred is isopropylalcohol or isobutanol.

A compound (IV-1) includes 3-amino-1,2,4-triazole-5-carboxylic acid and its alkyl ester derivatives (e.g., 3-amino-1,2,4-triazole-5-carboxylic acid methyl ester, 3-amino-1,2,4-triazole-5-carboxylic acid ethyl ester). Preferred is a compound wherein $R^5$ is hydrogen, 3-amino-1,2,4-triazole-5-carboxylic acid.

When a compound (IV-1) is an alkyl ester derivative of 3-amino-1,2,4-triazole-5-carboxylic acid, the reaction temperature should be controlled for preventing its ester part from converting to carboxylic acid.

Process B2

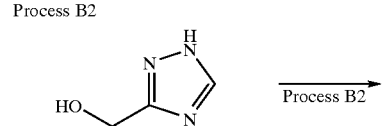

1, 2, 4-triazole-3-carboxylic acid

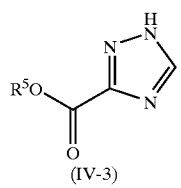

wherein $R^5$ is optionally substituted alkyl.

This scheme shows a process for the preparation of a compound (IV-3) which comprises esterifing 1,2,4-triazole-3-carboxylic acid prepared through the process B1 wherein $R^1$ is hydrogen.

A carboxylic acid can be esterified in accordance with the usual manner of reacting it with alcohol in the presence of an acid catalyst.

To a solution of 1,2,4-triazole-3-carboxylic acid in alcohol (e.g., methanol, ethanol, n-propanol, n-butanol, benzylalcohol) is added dropwise under cooling with stirring, thionylhalide (e.g., thionylchloride, thionylbromide). The mixture is stirred at 60 to 90° C. (preferably, approximately 70° C.) for 1 to 10 hours (preferably, approximately 4 hours). The solvent is removed under reduced pressure, and the residue was filtered off and washed with an appropriate organic solvent (e.g., ether, ethylacetate, n-hexane) to give the objective, a compound (IV-3).

A condensing agent such as DCC, EDC or the like can be used in a coupling reaction of carboxylic acid and alcohol.

Another method of an esterifing reaction includes a method reacting with halogenated alkyl (e.g., methyl iodide, ethylbromide) in the presence of a base, a method reacting with diazomethane or trimethyiscilyl diazomethane, a method reacting with alkene (e.g., isobutylene) or the like.

Process B3

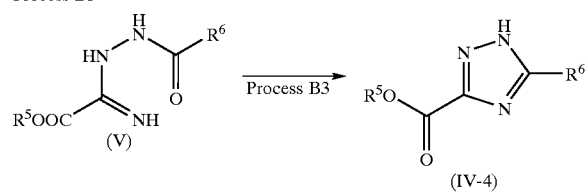

wherein $R^5$ is hydrogen or optionally substituted alkyl, $R^6$ is hydrogen, optionally substituted alkyl or optionally substituted aryl.

This scheme shows a process for the preparation of a compound (IV-4), which comprises a cyclization of a compound (V). In the past, this process should be performed at a high temperature (over melting point of a compound (V). This process can be performed by using the present invention at lower temperature, suitable to industrial production.

This process includes two kinds of methods, as shown below.

1) A Method Performed in the Presence of trialkylorthoester.

To a compound (V) are added trialkylorthoester (e.g., triethyl orthoformate, trimethyl orthoformate, triethyl orthoacetic acid, trimethyl orthoacetic acid, triethyl orthobenzoic acid, trimethyl orthobenzoic acid, triethyl orthoproprionic acid, trimethyl orthoproprionic acid) and an organic solvent (e.g., benzene, toluene, xylene). The mixture is stirred at 100 to 130° C. (preferably, 110 to 120° C.) for 1 to 10 hours (preferably, approximately 2.5 hours). A by-product, alcohol (produced from trialkylortho ester) is removed under a usual pressure. The distilled product is cooled at 0 to 20° C. (preferably, under 10° C.) and allowed to stand for 0.5 to 10 hours (preferably, approximately 1 hour). The objective, a compound (IV-4) can be obtained by filtering the precipitated crystal.

2) A Method Performed in the Presence of an Acid Catalyst.

To a compound (V) are added a catalytic amount (0.01–0.5, preferably, approximately 0.1 mole equivalent to a compound (V)) of an acid (e.g., methane sulfonic acid, benzene sulfonic acid, p-toluenesulfonic acid, p-toluenesulfonic acid mono hydrate, hydrochloric acid, sulfuric acid, nitric acid, polyphosphoric acid) and an organic solvent (e.g., dimethylformamide, N-methylpyrrolidone). The mixture is stirred at 100 to 130° C. (preferably, 110 to 120° C.) for 1 to 10 hours (preferably, approximately 3 hours). The reaction mixture is cooled at 0 to 20° C. (preferably, under 10° C.), mixed with an organic solvent (e.g., benzene, toluene, xylene) and stirred under cooling for 0.5 to 10 hours (preferably, approximately 1.5 hours). The objective, a compound (IV-4) can be obtained by a filtration of the precipitated crystal.

A compound (V) can be prepared by reacting thioformimidate with acylhydrazine (Collect. Czech. Chem. Commun., 49, 1984, 2492–2495, J. Heterocyclic Chem., 25, 651–654, 1998) as well as by reacting formimidate with acyl hydrazine.

A compound (V) includes ethyl β formyl oxalylamidrazone (a compound wherein $R^5$ is ethyl; and $R^6$ is hydrogen), methyl β formyl oxalylamidrazone (a compound wherein $R^5$ is methyl; and $R^6$ is hydrogen), ethyl β acetyloxalylamidrazone (a compound wherein $R^5$ is ethyl; and $R^6$ is methyl), methyl β acetyloxalylamidrazone (a compound wherein $R^5$ is methyl; and $R^6$ is methyl), ethyl β propionyloxalylamidrazone (a compound wherein $R^5$ is ethyl; and $R^6$ is ethyl), methyl β propionyloxalylamidrazone (a compound wherein $R^5$ is methyl; and $R^6$ is ethyl), β formyl oxalylamidrazone (a compound wherein $R^5$ and $R^6$ each is hydrogen), β acetyloxalylamidrazone (a compound wherein $R^5$ is hydrogen; and $R^6$ is methyl), β propionyloxalylamidrazone (a compound wherein $R^5$ is hydrogen; and $R^6$ is ethyl) or the like. Preferred is a compound wherein $R^5$ is alkyl, especially, ethyl β formyl oxalylamidrazone (a compound wherein $R^5$ is ethyl; and $R^6$ is hydrogen) or methyl β formyl oxalylamidrazone (a compound wherein $R^5$ is methyl; and $R^6$ is hydrogen).

Process B4

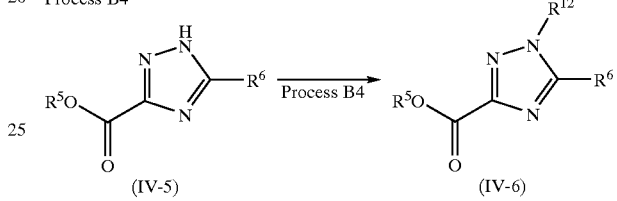

wherein $R^5$ is optionally substituted alkyl; $R^6$ is hydrogen, optionally substituted alkyl or optionally substituted aryl; $R^{12}$ is a group of the formula: —$R^7$ wherein $R^7$ is trityl, optionally substituted sulfamoyl or optionally substituted alkoxymethyl, a group of the formula: —C($OR^8$)$R^9$—$CHR^{10}R^{11}$ wherein $R^8$ is optionally substituted alkyl; $R^9$, $R^{10}$ and $R^{11}$ each is independently hydrogen or optionally substituted alkyl; or $R^8$ and $R^{10}$ may be taken together to form optionally substituted alkylene, or hydroxy methyl.

This process includes a process for the preparation of a compound (IV-6) which comprises introducing a protecting group ($R^{12}$) to a compound, (IV-5).

To a compound (IV-5) was added an organic solvent (e.g., tetrahydrofuran, dimethylformamide). To a compound (IV-5) is added one or more mole equivalent, preferably approximately 1.25 mole equivalent of a compound of the formula: $R^7X$ wherein $R^7$ is trityl, optionally substituted sulfamoyl or optionally substituted alkoxy methyl; and X is halogen, to a compound (IV-5), if desired, in the presence of one or more mole equivalent, preferably approximately 1.1 mole equivalent of a base (e.g., sodium hydride, N,N-dimethylacetamide) to a compound (IV-5). In another method, to a compound (IV-5) is added one or more mole equivalent, preferably approximately 1.1 mole equivalent of a compound of the formula: ($R^8O)R^9C$=$CR^{10}R^{11}$ wherein $R^8$ is optionally substituted alkyl; $R^9$, $R^{10}$ and $R^{11}$ each is independently hydrogen or optionally substituted alkyl; or $R^8$ and $R^{10}$ may be taken together to form optionally substituted alkylene to a compound (IV-5) in the presence of 0.01–0.5 mole equivalent, preferably approximately 0.03 mole equivalent of an acid (e.g., methane sulfonic acid, benzene sulfonic acid, p-toluenesulfonic acid, p-toluenesulfonic acid mono hydrate, hydrochloric acid, sulfuric acid, nitric acid) to a compound (IV-5).

The reaction mixture is stirred for 0.5 to 10 hours, preferably approximately 2 hours at room temperature, if desired, under heating. The mixture is extracted, washed, removed under reduced pressure and filtered to give the objective compound (IV-6).

When introducing tetrahydropyran-2-yl as a protecting group, a compound (IV-5) can be reacted with 3,4-dihydro-2H-pyran in the presence of an acid in THF. The acid can be used equivalent to a compound (IV-5) or in a catalytic amount. The acid includes p-toluene sulfonic acid, benzene sulfonic acid or the like.

When introducing 1-methoxy-1-methylethyl as a protecting group, a compound can be reacted with 2-methoxypropene in the presence of an acid in THF. The acid can be used equivalent to a compound (IV-5) or in a catalytic amount. The acid includes p-toluene sulfonic acid, benzene sulfonic acid or the like.

A compound of the formula: $R^7X$ includes tritylchloride, tritylbromide, methoxymethylchloride, methoxymethylbromide, ethoxymethylchloride, ethoxymethylbromide, sulfamoyl chloride, N,N-dimethylsulfamoyl chloride, sulfamoyl bromide, N,N-dimethylsulfamoyl bromide or the like.

A compound of the formula: $(R^8O)R^9C=CR^{10}R^{11}$ includes 3,4-dihydro-2H-pyran (a compound wherein $R^8$ and $R^{10}$ are taken together to form trimethylene; and $R^9$ and $R^{11}$ each is hydrogen), 2-methoxypropenone (a compound wherein $R^5$ and $R^9$ each is methyl; and $R^{10}$ and $R^{11}$ each is hydrogen), 2-ethoxypropene (a compound wherein $R^8$ is ethyl; $R^9$ is methyl; and $R^{10}$ and $R^{11}$ each is hydrogen), methylvinyl ether (a compound wherein $R^8$ is methyl; and $R^9$, $R^{10}$ and $R^{11}$ each is hydrogen), ethylvinyl ether (a compound wherein $R^8$ is ethyl; and $R^9$, $R^{10}$ and $R^{11}$ each is hydrogen), n-propylvinyl ether (a compound wherein $R^8$ is n-propyl; and $R^9$, $R^{10}$ and $R^{11}$ each is hydrogen), n-butylvinyl ether (a compound wherein $R^8$ is n-butyl; and $R^9$, $R^{10}$ and $R^{11}$ each is hydrogen), isobutylvinyl ether (a compound wherein $R^8$ is isobutyl; and $R^9$, $R^{10}$ and $R^{11}$ each is hydrogen) or the like.

Besides the above process, a hydroxymethyl group can be introduced as a protecting group to a compound (IV-5) by reacting with formaldehyde in accordance with a method described in A. R. Katritzky and K. Akutagawa, J. Org. Chem., 54, 2929 (1989).

Process B5

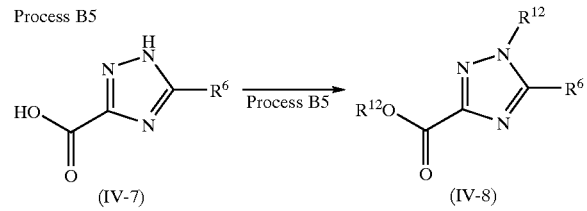

wherein $R^6$ is hydrogen, optionally substituted alkyl or optionally substituted aryl; and $R^{12}$ is a group of the formula: $-R^7$ wherein $R^7$ is trityl, optionally substituted sulfamoyl or optionally substituted alkoxy methyl, a group of the formula: $-C(OR^8)R^9-CHR^{10}R^{11}$ wherein $R^8$ is optionally substituted alkyl; $R^9$, $R^{10}$ and $R^{11}$ each is independently hydrogen or optionally substituted alkyl; or $R^8$ and $R^{10}$ may be taken together to form optionally substituted alkylene, or hydroxy group.

This process includes a process for the preparation of a compound VI-8) which comprises introducing protective groups ($R^{12}$) at two positions to a compound (IV-7). The introduction of a protecting group at two positions at the same time can reduce the number of steps, thus being efficient and useful for industrial production.

This step can be carried out as well as the above B-4) except doubling the amount of a base and a compound of the formula: $R^7X$, an acid and a compound of the formula:

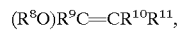

or formaldehyde.

A process for the preparation of substituted propenone derivatives is explained below.

Process C1

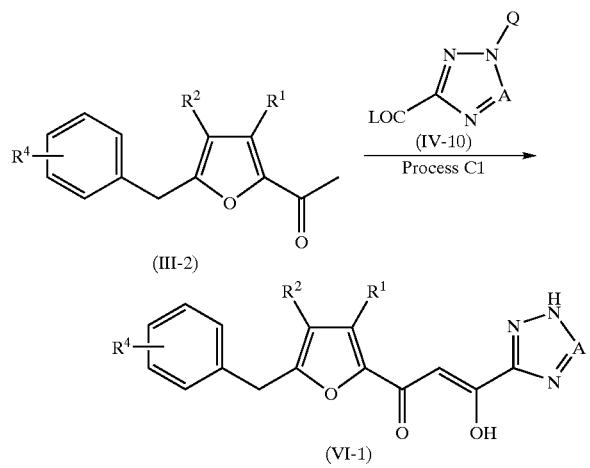

wherein $R^1$, $R^2$ and $R^4$ each is independently hydrogen, optionally substituted alkyl, optionally substituted alkoxy or halogen; A is $CR^6$ or N; $R^6$ is hydrogen, optionally substituted alkyl or optionally substituted aryl; L is a leaving group; and Q is a protecting group.

This scheme shows a process for the preparation of 1-[5-benzylfuran-2-yl]-3-hydroxy-3-(1H-1,2,4-triazole-3-yl)propenone derivatives from 2-acetyl-5-benzylfuran derivatives. This step can be carried out in the presence of a base, and followed by deprotection of a protecting group (Q) on tetrazolyl or triazolyl. In this step, a compound (III-2), a compound (III-1) wherein $R^3$ is methyl can be used.

A compound of the formula (III-2) includes 2-acetyl-5-benzylfuran, 2-acetyl-5-(4-methylbenzyl)furan, 2-acetyl-5-(4-methoxybenzyl)furan, 2-acetyl-5-(4-fluorobenzyl)furan, 2-acetyl-5-(4-chlorobenzyl)furan, 2-acetyl-5-(3-methylbenzyl)furan, 2-acetyl-5-(3-methoxybenzyl)furan, 2-acetyl-5-(3-fluorobenzyl)furan, 2-acetyl-5-(3-chlorobenzyl)furan or the like. Preferred is 2-acetyl-5-(4-fluorobenzyl)furan.

A compound of the formula (IV-10) includes 2-trityl-2H-tetrazole-5-carboxylic acid ethyl ester, 1-trityl-H-1,2,4-triazole-3-carboxylic acid methyl ester, 1-trityl-1H-1,2,4-triazole-3-carboxylic acid ethyl ester or the like. Preferred is 1-trityl-1H-1,2,4-triazole-3-carboxylic acid ethyl ester, 1-trityl-1H-1,2,4-triazole-3-carboxylic acid methyl ester.

A protecting group (Q) includes methoxymethyl, dialkoxy methyl, tert-butoxycarbonyl, 9-fluorenylmethoxycarbonyl, tosyl, trityl, allyl, formyl or the like. Moreover, a protecting group includes a group of the formula: $-R^7$ wherein $R^7$ is trityl, optionally substituted sulfamoyl or optionally substituted alkoxymethyl, a group of the formula: $-C(OR^8)R^9-CHR^{10}R^{11}$ wherein $R^8$ is optionally substituted alkyl; $R^9$, $R^{10}$ and $R^{11}$ each is independently hydrogen or optionally substituted alkyl; or $R^8$ and $R^{10}$ may be taken together to form optionally substituted alkylene, or hydroxy methyl. A deprotection of these protecting groups can be carried out, depending on the kind of protecting groups. The deprotection can be carried out by hydrolysis under an acidic condition or a basic condition.

A leaving group (L) includes alkoxy (methoxy, ethoxy, isopropoxy, tert-butoxy, biphenylmethoxy), heteroaryl (imidazolyl, tetrazolyl), cyano or the like. Preferred is methoxy or ethoxy.

A base includes sodium methoxide, sodium ethoxide, potassium tert-butoxide, n-butyllithium, lithiumbistrimethylscilylamide or the like. Preferred is sodium methoxide.

A reaction solvent includes dimethylformamide, tetrahydrofuran, dioxane, alcohols (e.g., methanol, ethanol, isopropylalcohol) or the like. A mixed solvent can be used as a reaction solvent. Preferred is tetrahydrofuran, methanol or a mixed solvent thereof.

A reaction temperature is –100 to 100° C., preferably –50 to 50° C.

A reaction time is 1 to 48 hours, preferably 1 to 24 hours.

A compound of the formula (III-2), a compound of the formula (IV-10) and a base can be added in any order. For example, a base may be added to a compound of the formula (III-2), and after a couple of minutes or hours a compound of the formula (IV-10) may be added thereto. As another method, abase (or a solvent comprising a base) may be added dropwise to a mixture of a compound of the formula (III-2) and a compound of the formula (IV-10).

Preferred is a process described in the following C2.

Process C2

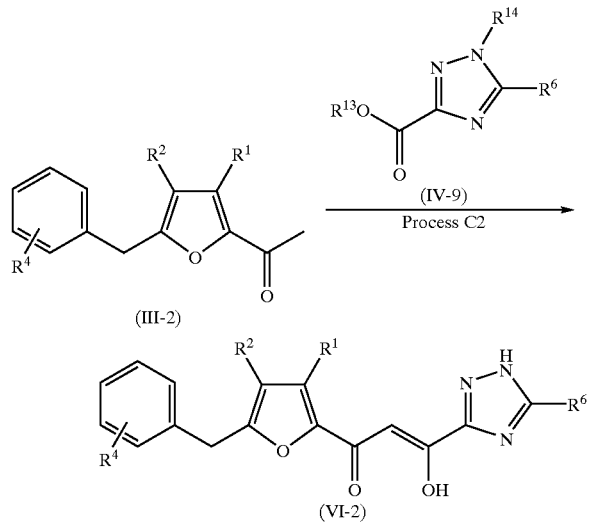

wherein $R^1$, $R^2$, and $R^4$ each is independently hydrogen, optionally substituted alkyl, optionally substituted alkoxy or halogen; $R^6$ is hydrogen, optionally substituted alkyl or optionally substituted aryl; $R^{13}$ is optionally substituted alkyl, a group of the formula: —$R^7$ wherein $R^7$ is trityl, optionally substituted sulfamoyl or optionally substituted alkoxymethyl, a group of the formula: —C(OR$^8$)R$^9$—CHR$^{10}$R$^{11}$ wherein $R^8$ is optionally substituted alkyl; $R^9$, $R^{10}$ and $R^{11}$ each is independently hydrogen or optionally substituted alkyl; or $R^8$ and $R^{10}$ may be taken together to form optionally substituted alkylene, or hydroxymethyl; and $R^{14}$ is a group of the formula —$R^7$ wherein $R^7$ is as defined above, a group of the formula: —C(OR$^8$)R$^9$—CHR$^{10}$R$^{11}$ wherein $R^8$, $R^9$, $R^{10}$ and $R^{11}$ are as defied above, or hydroxymethyl.

This scheme shows a process for the preparation of a compound of the formula (VI-2) which comprises reacting a compound of the formula (IV-9) obtained in process B4 or B5 with a compound of the formula (III-2) in the presence of a base and deprotecting $R^{14}$ on triazole.

A compound of the formula (III-2), a base, a reaction solvent, a reaction temperature and a reaction time are the same as Process C1.

A preferred compound of the formula (IV-9) includes a compound of the formula (IV-9):

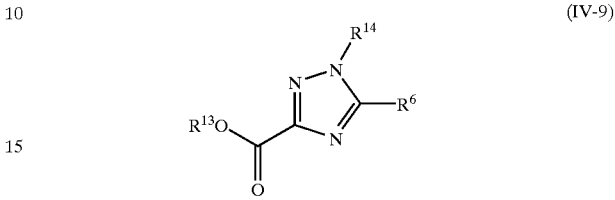

wherein $R^6$ is hydrogen or alkyl; $R^{13}$ is alkyl, a group of the formula: —$R^7$ wherein $R^7$ is trityl, optionally substituted sulfamoyl or alkoxy methyl, a group of the formula: —C(OR$^8$)R$^9$—CHR$^{10}$R$^{11}$ wherein $R^8$ is alkyl $R^9$, $R^{10}$ and $R^{11}$ each is independently hydrogen or alkyl; or $R^8$ and $R^{10}$ may be taken together to form alkylene, or hydroxymethyl; and $R^{14}$ is a group of the formula: —$R^7$ wherein $R^7$ is as defined above, a group of the formula: —C(OR$^8$)R$^9$—CHR$^{10}$R$^{11}$ wherein $R^8$, $R^9$, $R^{10}$ and $R^{11}$ are defied above, or hydroxymethyl; provided that a compound wherein $R^6$ is hydrogen; $R^{13}$ is methyl; and $R^{14}$ is trityl, a compound wherein $R^6$ is hydrogen; $R^{13}$ is methyl; and $R^{14}$ is tetrahydropyran-2-yl and a compound wherein $R^6$ is hydrogen; $R^{13}$ is ethyl; and $R^{14}$ is trityl are excluded. More Preferred is a compound wherein $R^6$ is hydrogen; $R^{13}$ is methyl or ethyl; and $R^{14}$ is tetrahydropyran-2-yl, hydroxymethyl, methoxymethyl, ethoxymethyl, N,N-dimethylsulfamoyl, (1-methoxy-1-methyl)ethyl, (1-ethoxy)ethyl, (1-ethoxy-1-methyl)ethyl, (1-n-propoxy)ethyl, (1-n-butoxy)ethyl or (1-isobutoxy)ethyl.

For example, a compound of the formula (IV-9) includes 1-trityl-1H-1,2,4-triazole-3-carboxylic acid methyl ester, 1-trityl-1H-1,2,4-triazole-3-carboxylic acid ethyl ester, 1-(tetrahydropyran-2-yl)-1H-1,2,4-triazole-3-carboxylic acid ethyl ester, 1-hydroxy methyl-1H-1,2,4-triazole-3-carboxylic acid ethyl ester, 1-methoxymethyl-1H-1,2,4-triazole-3-carboxylic acid ethyl ester, 1-[(1-methoxy-1-methyl)ethyl]-1H-1,2,4-triazole-3-carboxylic acid ethyl ester, 1-[(1-ethoxy)ethyl]1H-1,2,4-triazole-3-carboxylic acid ethyl ester, 1-[(1-ethoxy-1-methyl)ethyl]-1H-1,2,4-triazole-3carboxylic acid ethyl ester, 1-[(1-n-propoxy)ethyl]-1H-1,2,4-triazole-3-carboxylic acid ethyl ester, 1-[(1-n-butoxy)ethyl]-1H-1,2,4-triazole-3-carboxylic acid ethyl ester, 1-trityl-1H-1,2,4-triazole-3-carboxylic acid methyl ester, 1-(tetrahydropyran-2-yl)-1H-1,2,4-triazole-3-carboxylic acid methyl ester, 1-hydroxy methyl-1H-1,2,4-triazole-3-carboxylic acid methylester, 1-methoxymethyl-1H-1,2,4-triazole-3-carboxylic acid methyl ester, 1-[(1-methoxy-1-methyl)ethyl]-1H-1,2,4-triazole-3-carboxylic acid methyl ester, 1-[(1-ethoxy)ethyl]-1H-1,2,4-triazole-3-carboxylic acid methyl ester, 1-[(1-ethoxy-1-methyl)ethyl]-1H-1,2,4-triazole-3-carboxylic acid methyl ester, 1-[(1-n-propoxy)ethyl]-1H-1,2,4-triazole-3-carboxylic acid methyl ester, 1-[(1-n-butoxy)ethyl]-1H-1,2,4-triazole-3-carboxylic acid methyl ester or the like.

This process can be carried out as shown below. In an organic solvent (e.g., tetrahydrofuran, dioxane, diethylether) is dissolved a compound of the formula (III-2). 1.0 to 3.0 mole equivalent, preferably approximately 2 mole equivalent of a base described above to a compound of the formula (III-2) is added thereto at −80 to −10° C., preferably −30 to −25° C. The mixture is stirred at the same temperature for 1 to 10 hours, preferably approximately 1.5 hours. A solution of a compound of the formula (IV-9) in an organic solvent (e.g., tetrahydrofuran, dioxane, diethyl ether) is added thereto at −80 to −5° C. (preferably, −32 to −7° C.). The mixture is warmed up to the room temperature (approximately 25° C.) and stirred for 1 to 10 hours (approximately 2 hours). After that, the reaction mixture is poured into an acid (e.g., dilute hydrochloric acid) for neutralizing excess of a base, extracted with an organic solvent (e.g., methylene chloride, chloroform, ethylacetate), washed with water, concentrated under reduced pressure and filtered to give a crystal.

A protected derivative includes a compound of the formula (IV-7):

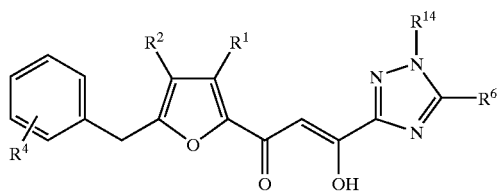

(VI-7)

wherein $R^1$, $R^2$ and $R^4$ each is independently hydrogen, optionally substituted alkyl, optionally substituted alkoxy or halogen; $R^6$ is hydrogen, optionally substituted alkyl or optionally substituted aryl; and $R^{14}$ is a group of the formula: —$R^7$ wherein $R^7$ is trityl, optionally substituted sulfamoyl or optionally substituted alkoxy methyl, a group of the formula: —$C(OR^8)R^9$—$CHR^{10}R^{11}$ wherein $R^8$ is alkyl; $R^9$, $R^{10}$ and $R^{11}$ each is independently hydrogen or optionally substituted alkyl; or $R^8$ and $R^{10}$ may be taken together to form alkylene, or hydroxymethyl. Preferred is a compound wherein $R^4$ is 4-fluoro; $R^1$, $R^2$ and $R^6$ each is hydrogen; and $R^{14}$ is trityl, tetrahydropyran-2-yl, hydroxymethyl, methoxymethyl, ethoxymethyl, N,N-dimethylsulfamoyl, (1-methoxy-1-methyl)ethyl, (1-ethoxy) ethyl, (1-ethoxy-1-methyl)ethyl, (1-n-propoxy)ethyl, (1-n-butoxy)ethyl or (1-isobutoxy)ethyl.

To a suspension of a crystal in an organic solvent (e.g., ethanol, dioxane) is added for removing a protecting group ($R^{14}$ on triazole) 0.01–10.0 mole equivalent, preferably 0.1–5.0 mole equivalent of an acid (e.g., hydrochloric acid, sulfuric acid, nitric acid) or a base (e.g., potassium carbonate, sodium hydroxide, potassium hydroxide, sodium hydrogencarbonate, sodium carbonate, sodium methoxide, sodium ethoxide) to a compound of the formula (III-2). The mixture is stirred at 0 to 100° C. (preferably 20 to 70° C.) for 1 to 10 hours (e.g., approximately 1 hour). An acid or a base can be used as a catalyst, which depends on a kind of protecting groups. When 1-methoxy-1-methylethyl group is used as a protecting group, it can be removed by using a catalytic amount of sulfuric acid.

When a base is used as a deprotecting agent, the objective compound of the formula (VI-2) can be obtained by cooling the reaction mixture and filtering the precipitated crystal.

When an acid is used as a deprotecting agent, a compound of the formula (VI-2) forms a salt with an acid. Therefore, the objective compound of the formula (VI-2) can be obtained by cooling the reaction mixture, adding 1.0–4.0 mole equivalent, preferably approximately 3.0 mole equivalent of a base (e.g., sodium hydroxide, potassium hydroxide, sodium carbonate, sodium hydrogencarbonate) for neutralizing excess of an acid to form a acid-free crystal, and filtering the precipitated crystal.

Impurities or the like can be removed by isolating a crystal as a salt. The obtained salt can be changed to a free form by adding a basic aqueous solution or the like after drying or without drying.

The obtained salt can be changed to a free form by adding to an aqueous solution or THF containing water without neutralizing it with a base, which depends on a kind of acids.

Preferred as a salt is a salt with hydrochloride or the like.

The obtained propenone derivatives can form keto-enol isomers or cis-trans isomers as shown below. In a solution, these isomers are at the equilibrium. Each isomer can be isolated as a crystal by selecting a crystallizing condition (e.g., crystallizing solvent, crystallizing temperature, time).

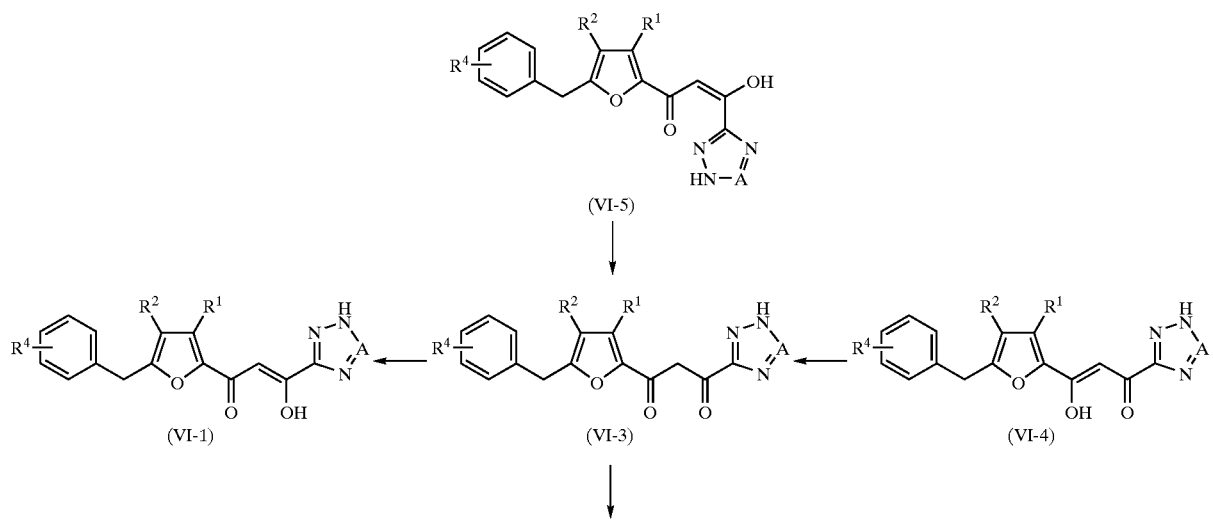

-continued

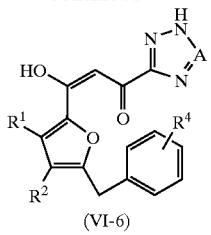

(VI-6)

wherein A is $CR^6$ or N; $R^6$ is hydrogen, optionally substituted alkyl or optionally substituted aryl; and $R^1$, $R^2$ and $R^4$ each is independently hydrogen, optionally substituted alkyl, optionally substituted alkoxy or halogen.

In the present specification, a compound of the formula (VI-1) includes all of the above isomers. On the other hand, an isomer having a structure of the formula (VI-1) means an isomer having a specific structure represented by the formula (VI-1).

When a compound of the formula (VI-1) is 1-[5-(4-fluorobenzyl)furan-2-yl]-3-hydroxy-3-(1H-1,2,4-triazole-3-yl)propenone (a compound of the formula (VI-1) wherein $R^1$ and $R^2$ each is hydrogen; $R^4$ is p-fluoro; and A is CH), the following three crystals (type I, type II and type III) can be obtained.

A Crystal (Type I)

It is determined by single crystal X-ray diffraction that a crystal (type I) is an isomer having a structure of the formula (VI-1). A crystal (type I) can be obtained by generally known crystallizing methods. For example, a crystal (type I) can be obtained by dissolving a compound of the formula (VI-1) in a warmed organic solvent, removing impurities by a plaited filter paper and cooling the solution. Any organic solvent, as far as a compound of the formula (VI-1) can be dissolved, can be used, for example, an organic solvent such as tetrahydrofuran, dimethylformamide, ethanol, methanol, isopropanol, ether, isopropylether, ethylacetate, methylene chloride, chloroform, dioxane or the like, a mixed solvent thereof (e.g., tetrahydrofuran/ethanol) or a solvent containing water (e.g., tetrahydrofuran/water). Considering a crystallizing yield or the like, preferred is an organic solvent, the solubility thereto much depends on temperature.

A crystal (Type II)

It is determined by single crystal X-ray diffraction that a crystal (type II) is an isomer having a structure of the formula (VI-4). A crystal (type II) can be obtained by dissolving a compound of the formula (VI-1) in an organic solvent at a lower concentration than that for obtaining a crystal (type I) and keeping it for several hours to several days. Preferred as an organic solvent for obtaining a crystal (type II) is an organic solvent which can gradually be vaporized even at room temperature (e.g., ethylacetate). A crystal (type II) can be precipitated by dissolving a compound of the formula (VI-1) in an organic solvent and naturally vaporizing the solvent at room temperature for several hours or several days.

A Crystal (type III)

It is determined by powder X-ray diffraction, infrared absorption spectrum and diffrential scanning calorimetry that this crystal is different from the above crystal (type I) and (type II). A crystal (type III) can be obtained by adding an alcohol (e.g., methanol, ethanol) or the like to a hydrochloride of a compound of the formula (VI-1) under heating and stirring, concentrating the alcohol under reduced pressure, adding an alcohol, repeating the same steps and filtering the precipitated crystal.

These crystals (type I), (type II) and (type III) are at the equilibrium in vivo and have anti-HIV activities. Therefore, all crystals are useful as anti-HIV agents.

Among these crystals (type I), (type II) and (type III), preferred is a crystal (type I), because it can easily be prepared and stably be provided.

These crystals can be identified by single crystal X-ray diffraction, powder X-ray diffraction, infrared absorption spectrum and diffrential scanning calorimetry. Each crystal can be identified by these instrumental analysis.

A crystalline substance can be identified by crystal parameter of single crystal X-ray diffraction such as unit cell constants and its space group. Unit cell constants are represented by lengths of its side faces, relative angles between its side faces and volume of itself. The lengths of its side faces are represented by a, b and c. The relative angles between its side faces are determined by α, β and γ. The volume of itself is determined by V. A unit cell is precisely explained in X-Ray Structure Determination; A Practical Guide, Macmirian, Staut and Jensen, New York (1968). Single crystal X-ray diffraction can be performed under the condition of CuKa, 1.54 Å (monochrometer), voltage 60 kV and electricity 300 mA. A measuring data includes experimental errors. For example, a data that a=32.432(2) Å means that a=32.432±0.002 Å, and generally includes that a=32.432±0.002×3 Å. Even if such experimental errors are put under consideration, characteristic peaks of single crystal X-ray diffraction of the above crystals are different from each other. Therefore, each crystal can be identified.

In powder X-ray diffraction, measuring peaks may include more or less experimental errors, which depend on a measuring equipment or measuring condition. For example, a data of a diffraction angle (2θ) may include experimental errors of approximately ±0.2, and even if using very precise equipment, may include experimental errors of approximately ±0.1. Therefore, experimental errors can be considered for identifying each crystal. Even if such experimental errors are taken into consideration, characteristic peaks of powder X-ray diffraction of the above crystals are different from each other. Therefore, each crystal can easily be identified. Powder X-ray diffraction can be performed under the condition of CuKα, 1.54 Å (monochrometer), voltage 40 kV and electricity 40 mA.

Each crystal can be identified by its characteristic absorption band of an infrared absorption spectrum. The absorption band may include a few experimental errors, which depend on measuring assemblies, measuring conditions and measuring methods such as a film method, a solution method, a nujol mull method and a KBr method. In a solution method, the absorption band may include a few experimental errors, which depend on a solvent to be used (e.g., $CCl_4$, $CS_2$, $CHCCl_3$, $CH_2CL_2$). When the structure of each crystal is identified, an experimental error should be considered. Even if an experimental error is considered, each characteristic absorption band and fingerprint region of each crystal are different form each other. Therefore, each crystal can be identified.

In diffrential scanning calorimetry, each crystal has its own characteristic peaks. These characteristic peaks can be determined by the obtained measuring charts. Each crystal can be identified by peaks (melting points) or change of energy of mass unit of a sample (ΔH). Approximately 1 to 3 mg of a sample is used for measuring. A scanning speed is 10.0° C./min. A measuring can be preformed between 25.0 to 200° C.

EXAMPLE

Examples of the above processes A to C are shown below. The scope of the present invention should not be limited to these examples.

Example 1

A process for the Preparation of 2-acetyl-5-(4-fluorobenzyl)furan

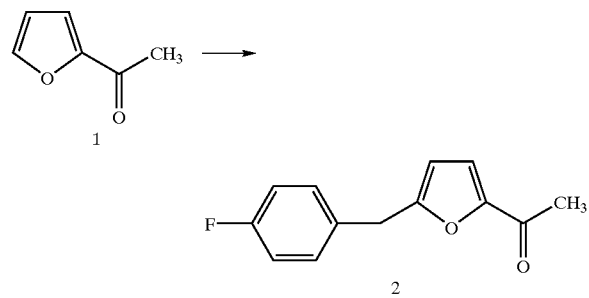

Example 1(1)

Example of Using Methylene Chloride as a Reaction Solvent

To a solution of 19.71 g (0.18 mol) of 2-acetylfuran in 120 ml of methylene chloride were added 42.9 ml (2.0 eq) of 4-fluorobenzylchloride and 36.6 g (1.5 eq) of zinc chloride. The mixture was refluxed for 12 hours. The precipitated crystal was filtered and washed with methylene chloride. The obtained solid was dissolved in water and extracted with ethylacetate. The organic layer was washed with water and a diluted aqueous solution of sodium hydrogencarbonate and dried over sodium sulfate. The solvent was evaporated under reduced pressure. The residue was recrystallized from n-hexane to give 16.4 g of 2-acetyl-5-(4-fluorobenzyl)furan. Yield: 42%. Mp: 27–29° C.

$^1$H NMR δ (CDCl$_3$): 2.43 (s, 3H), 4.01 (s, 2H), 6.09 (d, J=3.5 Hz, 1H), 6.96–7.26 (m, 5H).

Example 1(2)

Example Without a Reaction Solvent

A mixture of 9.2 g (83.4 mmol) of 2-acetylfuran, 20 ml (2.0 eq) of 4-fluorobenzylchloride and 22.8 g (2.0 eq) of zinc chloride were stirred at 25° C. for 20 hours. The stirring gradually became difficult due to the precipitate. The mixture was dissolved in water and extracted with ethylacetate. The organic layer was washed with water and a diluted sodium hydrogencarbonate aqueous solution and dried over sodium sulfate. The solvent was removed under deduced pressure. A fractional distillation under reduced pressure of the residue gave 9.6 g of 2-acetyl-5-(4-fluorobenzyl)furan. Yield: 53%. 2 mmHg/120–125° C.

Example 1(3)

Example of Using Water as a Reaction Solvent

To 258 g (0.94 mol) of a 50% aqueous solution of zinc chloride were added 69.3 g of water, 99.0 g (0.90 mol) of 2-acetylfuran and 260 g (1.80 mol) of 4-fluorobenzylchloride. The mixture was stirred at 85° C. for 6 hours. The reaction mixture was cooled and extracted with ethylacetate. The extract was washed with 1N hydrochloric acid, washed with an aqueous sodium hydrogencarbonate solution and removed under reduced pressure. The obtained residue was distilled under reduced pressure to give 145.4 g of crude 2-acetyl-5-(4-fluorobenzyl)furan (106–121° C./0.4 mmHg). The crude product was recrystallized from isopropylalcohol/n-hexane to give 84.4 g of 2-acetyl-5-(4-fluorobenzyl)furan. Yield: 43%.

Example 2

A process for the Preparation of 1H-1,2,4-triazole-3-carboxylic acid

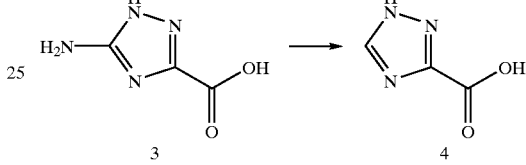

Example 2(1)

Example of Adding Diluted Hydrochloric Acid

To 2.74 g (20 mmol) of 3-amino-1,2,4-triazole-5-carboxylic acid were added 12 g of 6% diluted hydrochloric acid, 12.7 g of 13.5% aqueous hypophosphorous acid solution and 0.2 ml of isopropylalcohol. The mixture was warmed at 42° C. To the suspension was added, at 42 to 50° C. for approximately 25 minutes under stirring, 5.2 ml of an aqueous solution of 1.52 g (22 mmol) of sodium nitrite. After addition, the mixture was stirred at the same temperature for 30 minutes. The reaction mixture was cooled at approximately 5° C. and stirred for 30 minutes. The obtained suspension was filtered and washed with 15 ml of ice water. The obtained crystal was heated at 40° C. under reduced pressure to give 2.02 g of 1H-1,2,4-triazole-3-carboxylic acid. Yield: 89.4%.

Mp: 146–149° C.

$^1$H NMR(d6-DMSO) δ 8.53(s, 3H).

Example 2(2)

When a Diluted Hydrochloric Acid is not Added

To 2.74 g (20 mmol) of 3-amino-1,2,4-triazole-5-carboxylic acid were added 12.7 g of a 13.5% aqueous solution of hypophosphorous acid and 0.3 ml of isopropylalcohol. The mixture was warmed at 45° C. To the suspension was added, at 45 to 50° C. for 25 minutes under stirring, 5.2 ml of an aqueous solution of 1.52 g (22 mmol) of sodium nitrite. After addition, the mixture was stirred at the same temperature for 30 minutes. The mixture was cooled at approximately 5° C. for 30 minutes. The obtained suspension was filtered and washed with 15 ml of ice water. The obtained crystal was dried with heating at 40° C. under reduced pressure to give 2.16 g of 1H-1,2,4-triazole-3-carboxylic acid (2). Yield: 95.6%.

Mp: 145–150° C.

Example 3

A Process for the Preparation of 1H-1,2,4-triazole-3-carboxylic acid ethyl ester hydrochloride

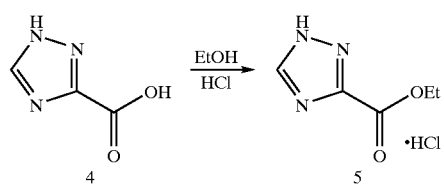

To 10 ml of a solution of 1.00 g (8.85 mmol) of 1H-1,2,4-triazole-3-carboxylic acid in 99.5% ethanol was added dropwise under stirring and cooling at 5° C. 1.58 g (13.2 mmol) of thionylchloride. The mixture was stirred under heating at 70° C. for 4 hours. Then, the solvent was removed under reduced pressure and the obtained residue was washed with 18 ml of ethylacetate. The obtained crystal was dried at room temperature under reduced pressure to give 1.00 g of 1H-1,2,4-triazole-3-carboxylic acid ethyl ester hydrochloride. Yield: 63.7%.

Mp: 115–120° C.

$^1$H NMR(d6-DMSO) δ 1.26(t, 3H, J=7.2 Hz) 4.28(q, 2H, J=7.2 Hz) 8.61(s, 1H); 9.19(s, 2H).

$^{13}$C NMR(d6-DMSO) δ 14.0, 60.8, 142.8, 145.6, 159.09.

Example 4

A Process for the Preparation of ethyl β-formyl oxalamidrazone

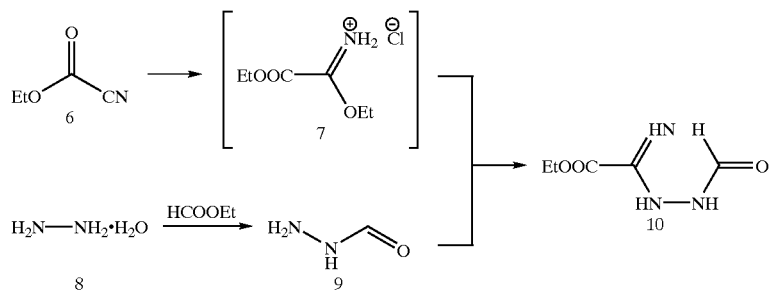

To a solution of 64.1 g (1.76 mol) of hydrogen chloride in 874 ml of ethylacetate was added 103 ml of anhydrous ethanol. The mixture was cooled at 5° C. 145 g (1.46 mol) of ethylcyanoformate was added thereto under stirring at 5–9° C. for approximately 10 minutes. After addition, the mixture was stirred at 0 to 10° C. for approximately 20 hours. To the reaction mixture was added under 10° C. 580 ml of methanol and the precipitated crystal of formimidate was dissolved therein. The solution was added dropwise under 10° C. for approximately 20 minutes to a solution of formylhydrazine in methanol (prepared from 872 ml of methanol, 73 g (1.46 mol) of hydrazine monohydrate and 119.2 g (1.6 mol) of ethylformate ester). After addition, the mixture was stirred at 5 to 10° C. for 1 hour. 702.4 g of a 10% aqueous solution of sodium hydroxide was added dropwise thereto at the same temperature for approximately 30 minutes to make the pH of the reaction solution pH 7. The neutralized solution was heated at 45° C. under reduced pressure and approximately 1850 ml of methanol was removed. The obtained residue was stirred at 5° C. for 1 hour and a crystal was precipitated. The precipitated crystal was filtered, washed with 244 ml of ice water and dried with heating at 40° C. under reduced pressure to give 130.97 g of ethyl β formyl oxalamidrazone. Yield: 56.2%.

Example 5

A Process for the Preparation of 1H-1,2,4-triazole-3-carboxylic acid ethyl ester

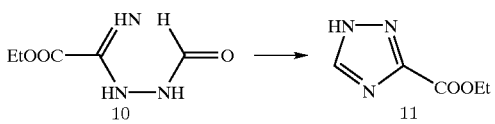

Example 5(1)

In the Presence of ortho triethylformate

To 130.97 g (0.82 mol) of ethyl β formyl oxalamidrazone were added 243.9 g (1.64 mol) of ortho triethylformate and 1310 ml of toluene. The mixture was refluxed at oil bath (110–120° C.) for 2.5 hours. After that, a side product, ethanol was removed approximately 200 g under usual pressure before the temperature of the mixture became approximately 100° C. The concentrated solution was cooled and the crystal was precipitated at 5–10° C. for 1 hour. The precipitated crystal was filtered, washed with 249 ml of iced toluene and dried with heating at 45° C. under reduced pressure to give 112 g of 1H-1,2,4-triazole-3-carboxylic acid ethyl ester. Yield: 96.8%.

Mp: 180–182° C.

$^1$H NMR(CDCl$_3$) δ 1.30(t, 3H, J=6.9 Hz) 4.22(q, 2H, J=6.9 Hz) 8.66(s, 1H).

Example 5(2)

Example in the Presence of p-toluenesulfonic acid

A mixture of 500 mg (3.42 mmol) of ethyl β formyl oxalamidrazone, 60 mg (0.32 mmol) of p-toluenesulfonic acid monohydrate and 1 ml of DMF were stirred with heating at 120° C. for 3 hours. The mixture was cooled at room temperature. 10 ml of toluene was added thereto and stirred under ice cooling for 1.5 hours. The precipitated crystal was filtered, washed with 9 ml of iced toluene and dried with heating 45° C. under reduced pressure to give 389 mg of 1H-1,2,4-triazole-3-carboxylic acid ethyl ester. Yield: 87.8%.

Example 6

A Process for the Preparation of 1-(tetrahydropyran-2-yl)-1,2,4-triazole-3-carboxylic acid ethyl ester

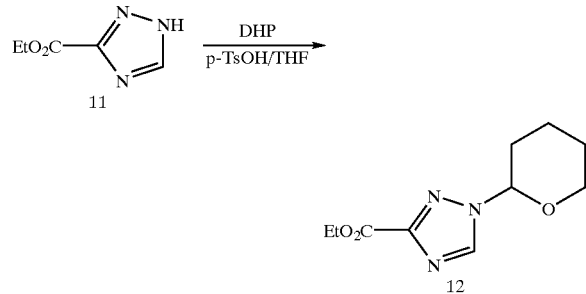

Example 6(1)

Example of Using p-toluenesulfonic acid

To a suspension of 1.25 g (8.86 mmol) of 1H-1,2,4-triazole-3-carboxylic acid ethyl ester in 4 ml of THF was added 51 mg (0.27 mmol) of p-toluenesulfonic acid monohydrate. To the suspension was added at room temperature with stirring 1 ml (11 mmol) of 3,4-dihydro-2H-pyran. The mixture was stirred at room temperature for 2 hours and extracted with 15 ml of ethylacetate. The extract was washed with a saturated aqueous solution of sodium hydrogencarbonate and dried over $Na_2SO_4$. The solvent was concentrated under reduced pressure to give 1.98 g of an oil. The obtained oil was purified with silica gel chromatography (eluate: ethylacetate) to give 1.81 g of 1-(tetrahydropyran-2-yl)-1,2,4-triazole-3-carboxylic acid ethyl ester as colorless oil. Yield: 91%.

NMR(CDCl$_3$) δ 1.43(t, 3H, J=7.2 Hz) 1.66–1.74(m, 3H) 2.01–2.05(m, 2H) 2.21–2.25(m, 1H) 3.72–3.77(m, 1H) 4.07–4.11(m, 1H) 4.48(q, 2H, J=7.2 Hz) 5.54(dd, 1H, J=2.7, 9.0 Hz) 8.37(s, 1H).

IR(neat) 1738 cm$^{-1}$.

Example 6(2)

Example of Using benzene sulfonic acid 1-(Tetrahydropyran-2-yl)-1,2,4-triazole-3-carboxylic acid ethyl ester was obtained by using a catalytic amount of benzene sulfonic acid in place of p-toluenesulfonic acid monohydrate in Example 6(1).

Example 7

A Process for the Preparation of 1-trityl-1,2,4-triazole-3-carboxylic acid ethyl ester

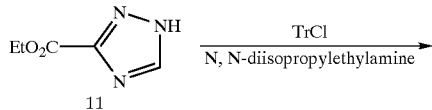

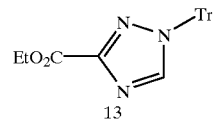

In 60 ml of DMF was dissolved 7.62 g (54 mmol) of 1H-1,2,4-triazole-3-carboxylic acid ethyl ester. To the solution were added at room temperature 14 g (108 mmol) of N,N-diisopropylethylamine and 15.8 g (56.7 mmol) of tritylchloride. The mixture was stirred for 2 hours. 300 ml of water and 300 ml of ethylacetate were added thereto. The crystal was filtered, dissolved in 150 ml of chloroform, washed with water and dried. The solvent was removed. The residue was crystallized from ether to give 8.91 g of the titled compound. The ethylacetate layer was washed with water, dried and evaporated. The residue was crystallized from ether to give 4.73 g of the titled compound. 13.64 g of 1-trityl-1,2,4-triazole-3-carboxylic acid ethyl ester was totally obtained. Yield: 66%.

NMR(CDCl3) δ: 1.41(3H, t, J=7.2 Hz), 4.45(2H, q, J=7.2 Hz), 7.11–7.13(6H, m), 7.32–7.36, 8.01(1H, s).

Example 8

Process for the Preparation of 1-(N,N-dimethylsulfamoyl)-1,2,4-triazole-3-carboxylic acid ethyl ester

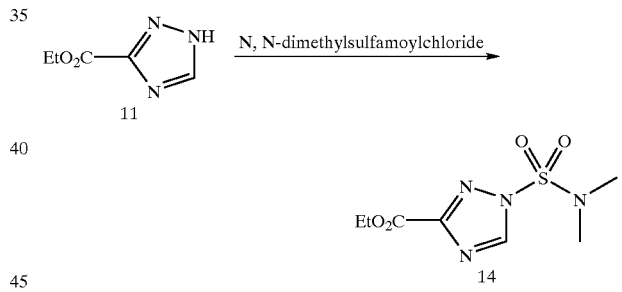

To a solution of 1.02 g (7.23 mmol) of 1H-1,2,4-triazole-3-carboxylic acid ethyl ester in 6 ml of DMF was added 1.46 g (1.44 mmol) of triethylamine. To the solution was added dropwise with stirring under ice-cooling 1.14 g (7.94 mmol) of dimethylsulfamoyl chloride. The mixture was stirred at room temperature for 8 hours. 30 ml of Water was added thereto and extracted with 20 ml of ethylacetate. The extract was washed with a saturated aqueous solution of sodium hydrogencarbonate and water, dried over Na2SO$_4$ and evaporated under reduced pressure to give an oil. The obtained oil was purified with silica gel chromatography (eluate: hexane/ethylacetate=2:1) to give 1.46 g of 1-dimethylsulfamoyl-1,2,4-triazole-3-carboxylic acid ethyl ester as a white crystal. Yield: 82%.

Mp: 78.5–81.5° C.

NMR(CDCl$_3$) δ 1.44(t, 3H, J=7.2 Hz) 3.06(s, 6H) 4.50(q, 2H, J=7.2 Hz) 8.63(s, 1H).

Example 9(1)

A Process for the Preparation of 1-(1-methoxy-1-methylethyl)-1H-1,2,4-triazole-3-carboxylic acid ethyl

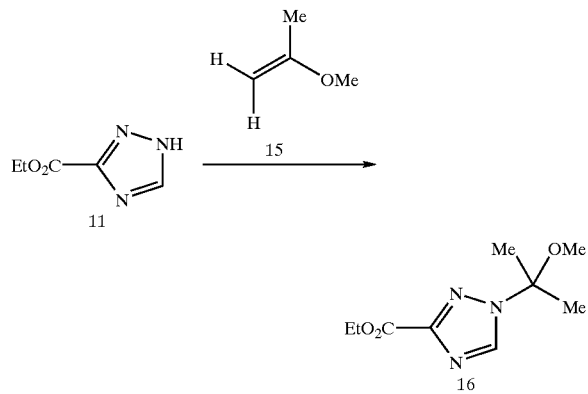

To a slurry of 0.71 g (5 mmol) of 1H-1,2,4-triazole-3-carboxylic acid ethyl ester in 3.5 ml of THF was added 26 mg (3 mol %) of benzene sulfonic acid monohydrate. 0.72 g (10 mmol) of 2-methoxypropene was added dropwise thereto under ice cooling. The mixture was stirred at room temperature for 2 hours. The reaction mixture was extracted with 15 ml of ethylacetate, washed with a saturated aqueous solution of sodium bicarbonate, dried over MgSO$_4$ to give yellow oil. The oil was purified with silica gel chromatography (eluate: hexanelethylacetate=1:1) to give 0.50 g of 1-(1-methoxy-1-methylethyl)-1H-1,2,4-triazole-3-carboxylic acid ethyl as a pale yellow oil. Yield: 47%.

NMR(CDCl$_3$) δ 1.44(t, 3H J=7.2 Hz) 1.84(s, 6H) 3.20(s, 3H) 4.49(q, 2H J=7.2 Hz) 8.38(s, 1H).

HPLC tR=26.7 min; Column: Inertsil ODS-3 (5 μm) 4.6×250 mm; Mobile Phase: phosphate buffer (pH7)/acetonitrile (85:15); Flow Rate: 1.0 mL/min Detector: 205 nm.

Compounds described in the following Example 9(2) to 9(5) were prepared in accordance with the same manner of Example 9(1).

Example 9(2)

1-(1-Ethoxyethyl)-1H-1,2,4-triazole-3-carboxylic acid ethyl

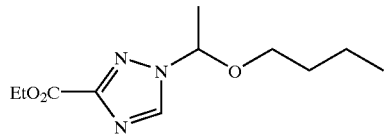

NMR(CDCl$_3$) δ 1.20(t, 3H J=7.2 Hz) 1.45(t, 3H J=7.2 Hz) 1.73 (d, 3H J=6.0 Hz) 3.41–3.62(m, 2H) 4.50(q, 2H J=7.2 Hz) 5.69(q, 1H J=6.0 Hz) 8.36(s, 1H).

Mp: 59–60° C.

Example 9(3)

1-(1-Isobutoxyethyl)-1H-1,2,4-triazole-3-carboxylic acid ethyl

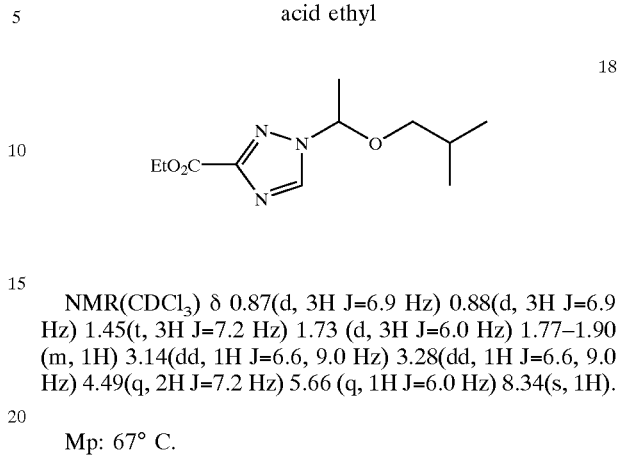

NMR(CDCl$_3$) δ 0.87(d, 3H J=6.9 Hz) 0.88(d, 3H J=6.9 Hz) 1.45(t, 3H J=7.2 Hz) 1.73 (d, 3H J=6.0 Hz) 1.77–1.90 (m, 1H) 3.14(dd, 1H J=6.6, 9.0 Hz) 3.28(dd, 1H J=6.6, 9.0 Hz) 4.49(q, 2H J=7.2 Hz) 5.66 (q, 1H J=6.0 Hz) 8.34(s, 1H).

Mp: 67° C.

Example 9(4)

1-(1-Butoxyethyl)-1H-1,2,4-triazole-3-carboxylic acid ethyl

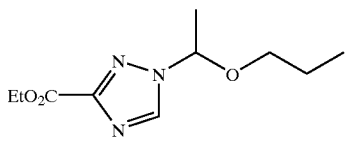

NMR(CDC$_3$) δ 0.88(t, 3H J=6.9 Hz) 1.25–1.40(m, 2H) 1.45(t, 3H J=7.2 Hz) 1.45–1.60 (m, 2H) 1.73(d, 3H J=6.0 Hz) 3.34–3.42 (m, 1H) 3.46–3.54 (m, 1H) 4.50(q, 2H J=7.2 Hz) 5.67 (q, 1H J=6.0 Hz) 8.35(s, 1H).

Mp: 42–43° C.

Example 9(5)

1-(1-Propoxyethyl)-1H-1,2,4-triazole-3-carboxylic acid ethyl

NMR(CDCl$_3$) δ 0.89(t, 3H J=6.9 Hz) 1.45(t, 3H J=7.2 Hz) 1.45–1.60 (m, 2H) 1.73(d, 3H J=6.0 Hz) 3.34–3.42 (m, 1H) 3.46–3.54 (m, 1H) 4.50(q, 2H J=7.2 Hz) 5.67 (q, 1H J=6.0 Hz) 8.35(s, 1H).

Mp: 31–32° C.

Example 10

A Process for the Preparation of 1-[5-(4-Fluorobenzyl)furan-2-yl]-3-hydroxy-3-(1H-1,2,4-triazole-3-yl)propenone

Example 10(1)

Example of Using Trityl as a Protecting Group

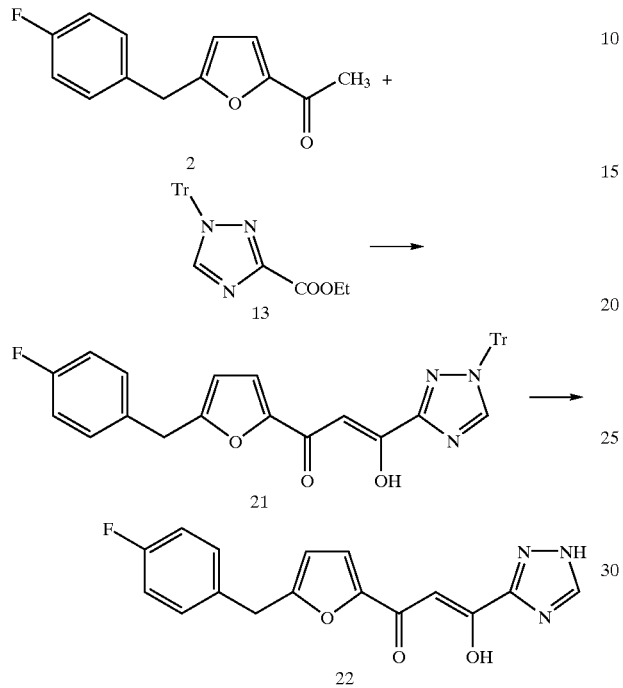

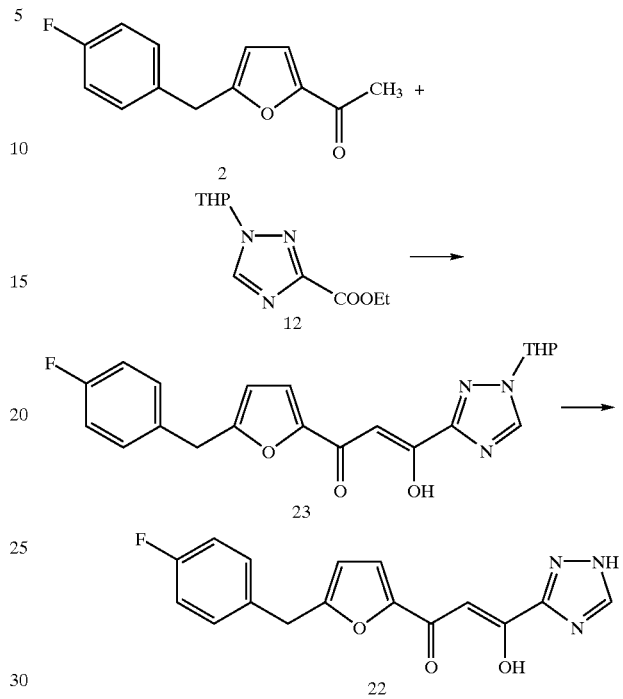

To a solution of 624 g (2.86 mol) of 5-(4-fluorobenzyl)-2-acetylfuran in 3.0 L of tetrahydrofuran was added at −32 to −25° C. 5.72 L (2.0 eq) of a solution of 1.0 M lithium bis(trimethylsilyl)amide in tetrahydrofuran. The mixture was stirred at the same temperature for 1.5 hours. 11.2 L of a solution of 1.26 kg (1.15 eq) of 1-trityl-3-ethoxycorbonyl-1,2,4-triazole in tetrahydrofuran was added thereto at −32 to −7° C. The reaction mixture was stirred at 25° C. for 2 hours, poured into diluted hydrochloric acid and extracted with ethylacetate. The organic layer was washed with water and evaporated under reduced pressure to give a slurry. The crystal was filtered to give 1.53 kg of a protective form. Yield: 95.8%.

The crystal was suspended in 7.5 L of dioxane and mixed with 2.74 L (3.0 eq) of 1.5 N hydrochloric acid. The mixture was stirred at 70° C. for 1 hour. After cooling, 2.74 L (3.0 eq) of 1.5 N sodium hydroxide was added thereto and the precipitated crystal was filtered. The crystal was suspended in ethylacetate and dissolved in a diluted aqueous solution of sodium hydroxide. After the separation of water layer, an aqueous solution was acidified with concentrated hydrochloride to pH 4. The precipitated crystal was filtered and recrystallized from tetrahydrofuran/ethylalcohol to give 548 g of the titled compound. Yield: 64%.

Mp: 183–185° C.

Elementary analysis for $C_{16}H_{12}FN_3O_3$; Calcd (%): C, 61.34; H, 3.86; N, 13.41; F, 6.06. Found (%): C, 61.22; H, 3.72; N, 13.41; F, 6.03.

NMR($d_6$-DMSO) δ 4.15(2H, s), 6.47(1H, d, J=3.3 Hz), 6.93(1H, s), 7.17(2H, t, J=9.0 Hz), 7.31–7.37(2H, m), 7.50 (1H, d, J=3.3 Hz), 8.70(1H, brs).

Example 10(2)

Example of Using tetrahydropyran-2-yl as a Protecting Group

Example 10(2-1)

To a solution of 0.70 g (3.2 mmol) of 2-acetyl-5-(4-fluorobenzyl)furan and 0.72 g (3.2 mmol) of 1-(tetrahydropyran-2-yl)-1-1,2,4-triazole-3-carboxylic acid ethyl ester in 7 ml of THF was added dropwise under ice-cooling 0.64 g (3.2 mmol) of a 28% solution of sodium methoxide in methanol. The mixture was stirred at room temperature for 14 hours. The reaction mixture was mixed with 20 ml of a 1.8% aqueous solution of acetic acid and extracted with 30 ml of ethylacetate. The extract was washed with a saturated sodium hydrogencarbonate aqueous solution and water, dried over $Na_2SO_4$ and evaporated under reduced pressure to give 1.4 g of oil. The obtained oil was crystallized from isopropylalcohol to give 0.77 g of 1-[5-(4-fluorobenzyl)furan-2-yl]-3-hydroxy-3-[1-(tetrahydropyran-2-yl)-1,2,4-triazole-3-yl]propenone as a pale yellow crystal. Yield: 61%.

Mp: 128–130° C.

NMR(CDCl₃) δ 1.66–1.76(m, 3H) 2.03–2.08(m, 2H) 2.21–2.27(m, 1H) 3.70–3.78(m, 1H) 3.99–4.13(m, 1H) 4.04 (s, 2H) 5.55(dd, 1H, J=3.0,9.0 Hz) 6.15(d, 1H, J=3.3 Hz) 6.99–7.25(m, 5H) 7.02(s, 1H) 8.36(s, 1H).

A mixture of 0.40 g (1 mmol) of 1-[5-(4-fluorobenzyl) furan-2-yl]-3-hydroxy-3-[1-(tetrahydropyran-2-yl)-1,2,4-triazole-3-yl]propenone, 2 ml of 1 N diluted hydrochloric acid and 2 ml of methanol was stirred at 75° C. for 2 hours. The reaction mixture was cooled to room temperature and stirred under ice cooling for 15 minutes. The precipitated crystal was filtered and washed with methanol to give 0.29 g of 1-[5-(4-fluorobenzyl)furan-2-yl])3-hydroxy-3-(1H-1,2,4-triazole-3-yl)propenone as a pale yellow crystal. Yield: 93%.

Example 10(2-2)

1-[5-(4-Fluorobenzyl)furan-2-yl]-3-hydroxy-3-[1-(tetrahydropyran-2-yl)-1,2,4-triazole-3-yl]propenone was prepared in accordance with the same method of Example 10(2-1) and reacted with concentrated hydrochloric acid/isopropylalcohol to isolate 1-[5-(4-fluorobenzyl)furan-2-yl]-3-hydroxy-3-(1H-1,2,4-triazole-3-yl)propenone hydrochloride. The obtained hydrochloride salt was dissolved in aqueous THF. The precipitated crystal was filtered to give 1-[5-(4-fluorobenzyl)furan-2-yl]-3-hydroxy-3-(1H-1,2,4-triazole-3-yl)propenone.

Example 10(2-3)

1-[5-(4-Fluorobenzyl)furan-2-yl]-3-hydroxy-3-[1-(tetrahydropyran-2-yl)-1,2,4-triazole-3-yl]propenone was prepared in accordance with the same method of Example 10(2-1), reacted with concentrated hydrochloric acid/methanol to isolate 1-[5-(4-fluorobenzyl)furan-2-yl]-3-hydroxy-3-(1H-1,2,4-triazole-3-yl)propenone hydrochloride. The obtained hydrochloride salt was dissolved in aqueous THF and neutralized with one mole equivalent of sodium carbonate. The precipitated crystal was filtered to give 1-[5-(4-fluorobenzyl)furan-2-yl]-3-hydroxy-3-(1H-1,2,4-triazole-3-yl)propenone.

Example 11(1)

Process for the Preparation of 1-[5-(4-fluorobenzyl)furan-2-yl]-3-hydroxy-3-[1-(1-methoxy-1-methylethyl)-1H-1,2,4-triazole-3-yl]propeuone

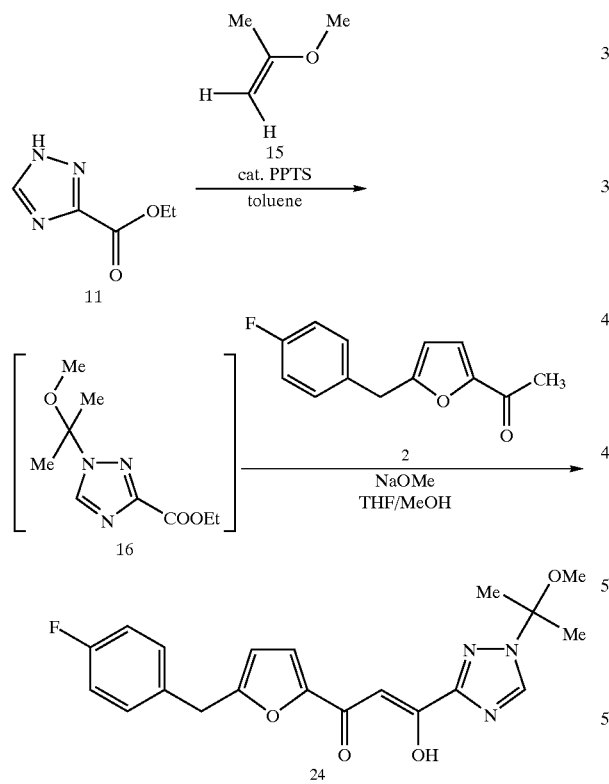

A slurry of 7.06 g (50 mmol) of 1H-1,2,4-triazole-3-carboxylic acid ethyl ester in 35 ml of toluene was added 0.38 g (3 mol %) of p-toluenesulfonic acid pyridinium salt monohydrate. 4.69 g (65 mmol) of 2-methoxypropene was added dropwise at room temperature thereto. The mixture was stirred at 45° C. for 2 hours. After that, 10.91 g (50 mmol) of 2-acetyl-5-(4-fluorobenzyl)furan and 35 ml of THF were added thereto and then 13.5 ml (65 mmol) of a 28% solution of sodium methoxide in methanol was added dropwise under ice-cooling. The reaction mixture was warmed up to 60° C. and stirred for 3 hours. The reaction mixture was cooled to room temperature and kept standing overnight. To the solution was added dropwise under ice cooling 28.5 g of a 13.7% solution of acetic acid. The organic layer was separated. The extract was washed with 28.5 g of 5% brine, concentrated at 45° C. under 50 mmHg to give 26.71 g of an oil. The residue was crystallized from 42 ml of isopropylalcohol to give 14.58 g of 1-[5-(4-fluorobenzyl)furan-2-yl]-3-hydroxy-3-[1-(1-methoxy-1-methylethyl)-1H-1,2,4-triazole-3-yl]propenone as yellow crystal. Yield: 75.7%.

NMR(CDCl$_3$) δ 5 1.86(s, 6H) 3.22(s, 3H) 4.05(s, 2H) 6.16(d, 1H, J=3.3 Hz) 6.99–7.05(m, 2H) 7.02(s, 1H) 7.20–7.25(m, 3H) 8.38(s, 1H).

Mp: 111° C.

The following compounds described in Example 11(2) to 11(5) were prepared in accordance with the same manner of Example 11(1).

Example 11(2)

1-[5-(4-Fluorobenzyl)furan-2-yl]-3-hydroxy-3-[1-(1-ethoxyethyl)-1H-1,2,4-triazole-3-yl]propenone

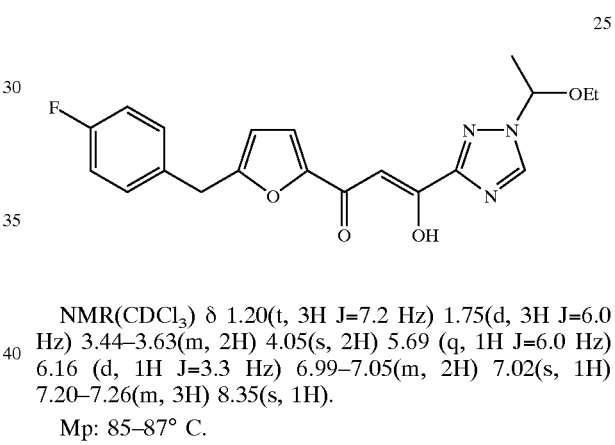

NMR(CDCl$_3$) δ 1.20(t, 3H J=7.2 Hz) 1.75(d, 3H J=6.0 Hz) 3.44–3.63(m, 2H) 4.05(s, 2H) 5.69 (q, 1H J=6.0 Hz) 6.16 (d, 1H J=3.3 Hz) 6.99–7.05(m, 2H) 7.02(s, 1H) 7.20–7.26(m, 3H) 8.35(s, 1H).

Mp: 85–87° C.

Example 11(3)

1-[5-(4-Fluorobenzyl)furan-2-yl]-3-hydroxy-3-[1-(1-isobutoxyethyl)-1H-1,2,4-triazole-3-yl]propenone

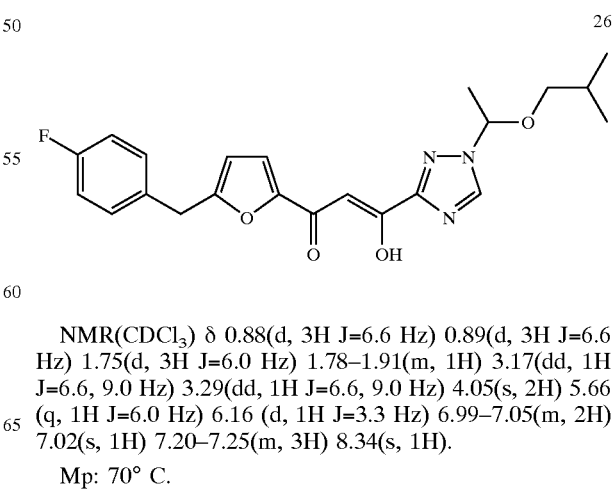

NMR(CDCl$_3$) δ 0.88(d, 3H J=6.6 Hz) 0.89(d, 3H J=6.6 Hz) 1.75(d, 3H J=6.0 Hz) 1.78–1.91(m, 1H) 3.17(dd, 1H J=6.6, 9.0 Hz) 3.29(dd, 1H J=6.6, 9.0 Hz) 4.05(s, 2H) 5.66 (q, 1H J=6.0 Hz) 6.16 (d, 1H J=3.3 Hz) 6.99–7.05(m, 2H) 7.02(s, 1H) 7.20–7.25(m, 3H) 8.34(s, 1H).

Mp: 70° C.

Example 11(4)

1-[5-(4-Fluorobenzyl)furan-2-yl]-3-hydroxy-3-[1-(1-butoxyethyl)-1H-1,2,4-triazole-3-yl]propenone

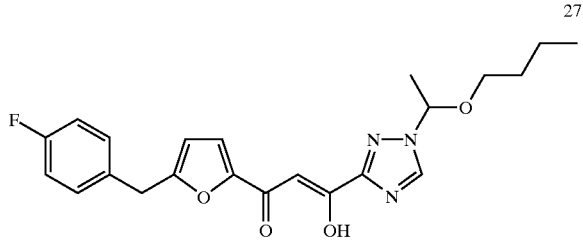

NMR(CDCl₃) δ 0.89(t, 3H J=7.2 Hz) 1.27–1.37(m, 2H) 1.50–1.59(m, 2H) 1.75(d, 3H J=6.0 Hz) 3.47–3.53(m, 2H) 4.05(s, 2H) 5.67 (q, 1H J=6.0 Hz) 6.16 (d, 1H J=3.3 Hz) 6.99–7.05(m, 2H) 7.02(s, 1H) 7.20–7.26(m, 3H) 8.34(s, 1H).

IR(neat)=3117, 2960, 2935, 2874, 1736, 1714, 1606 cm⁻¹.

Example 11(5)

1-[5-(4-Fluorobenzyl)furan-2-yl]-3-hydroxy-3-[1-(1-propoxyethyl)-1H-1,2,4-triazole-3-yl]propenone

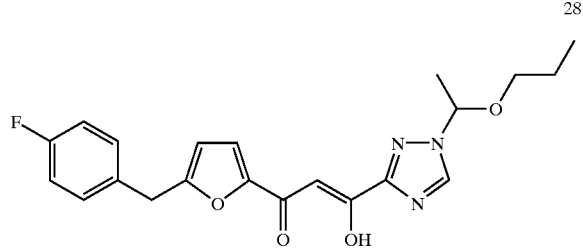

NMR(CDCl₃) δ 0.90(t, 3H J=7.2 Hz) 1.53–1.65(m, 2H) 1.75(d, 3H J=6.0 Hz) 3.33–3.41(m, 1H) 3.44–3.52(m, 1H) 4.05(s, 2H) 5.68 (q, 1H J=6.0 Hz) 6.16 (d, 1H J=3.3 Hz) 6.99–7.05(m, 2H) 7.02(s, 1H) 7.20–7.25(m, 3H) 8.35(s, 1H).

Mp: 67–68° C.

Example 12

1-[5-(4-Fluorobenzyl)furan-2-yl]-3-hydroxy-3-(1H-1,2,4-4-triazole-3-yl)propenone

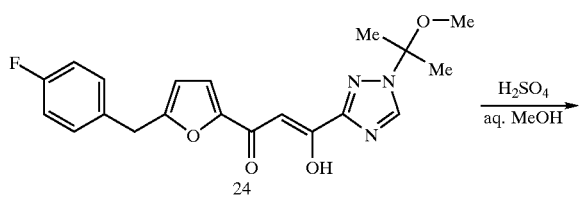

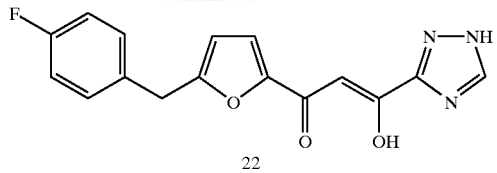

A solution of 4 g (10.4 mmol) of 1-[5-(4-fluorobenzyl)furan-2-yl]-3-hydroxy-3-1-(1-methoxy-1-methylethyl)-1,2,4-triazole-3-yl]propenone in 10.2 ml of a 2% aqueous solution of sulfuric acid and 30 ml of methanol were stirred at 60° C. for 1 hour. The solution was cooled and stirred at room temperature for 1 hour. A precipitated crystal was filtered off and washed with 20 ml of 75% methanol to give 2.72 g of 1-[5-(4-fluorobenzyl)furan-2-yl]-3-hydroxy-3-(1H-1,2,4-triazole-3-yl)propenone as a pale yellow crystal.

Yield: 83.4%.

1-[5-(4-fluorobenzyl)furan-2-yl]-3-hydroxy-3-(1NH-1,2,4-triazole-3-yl)propenone was prepared from a compound obtained in Example 11(2)–11(6) after deprotection such as Example 12.

Example 13(1)

A Preparation of a Crystal (Type I) of 1-[5-(4-fluorobenzyl)furan-2-yl]-3-hydroxy-3-(1H-1,2,4-triazole-3-yl)propenone 712 g of 1-[5-(4-fluorobenzyl)furan-2-yl]-3-hydroxy-3-(1H-1,2,4-triazole-3-yl)propenone was dissolved in 7 L of THF under heating. The obtained solution was filtered and washed with 2 L of THF. The obtained solution was concentrated under reduced pressure and 17 L. of 99.5% EtOH was gradually added thereto. The solution was concentrated under reduced pressure to give 8.3 kg of the residue. The obtained slurry was stirred for 1 hour under water-cooling and filtered to give 548 g of a crystal (type I). According to single crystal X-ray diffraction, a crystal (type I) was a isomer having a chemical structure of the formula:

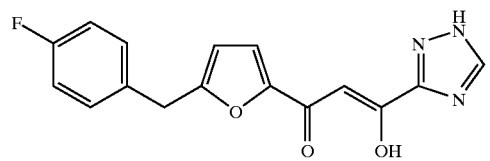

Elementary analysis for C₁₆H₁₂FN₃O₃. Calcd (%): C, 61.34; H, 3.86; N, 13.41; F, 6.06. Found (%): C, 61.22; H, 3.72; N, 13.41; F, 6.03.

| Crystal parameters of single crystal X-ray diffraction | |
|---|---|
| Unit cell constants: | a = 32.432(2)Å |
| | b = 10.886(2)Å |
| | c = 7.960(2)Å |
| | α = 90.00° |
| | β = 90.00° |
| | γ = 90.00° |
| | V = 2810(1)Å³ |
| | Z = 8 |

-continued

| Space group: Pbca | |
|---|---|
| Density: 1.481 g/cm³ | |

Diffraction angles (2θ) and intensities of main peaks of powder X-ray diffraction of a crystal (type I)

| Diffraction angle (2θ) | Intensity |
|---|---|
| 20.380 | 5945 |
| 21.280 | 5455 |
| 21.340 | 4958 |
| 23.140 | 4053 |
| 23.360 | 7218 |
| 23.540 | 8173 |
| 25.860 | 4615 |
| 27.460 | 4138 |
| 27.500 | 4068 |
| 28.100 | 5143 |
| 28.180 | 4980 |
| 29.400 | 4528 |
| 29.480 | 4848 |

Differential scanning calorimetry

| Peak (° C.) | ΔH (J/g) |
|---|---|
| 185.831 | 149.181 |

Example 13(2)

A Preparation of a Crystal (Type I) of 1-[5-(4-fluorobenzyl)furan-2-yl]-3-hydroxy-3-(1H-1,2,4-triazole-3-yl)propenone 4 g of 1-[5-(4-fluorobenzyl)furan-2-yl]-3-hydroxy-3-(1H-1,2,4-triazole-3-yl)propenone was dissolved under heating in 21.2 ml of THF/$H_2O$ (50:3). The obtained solution was filtered and 40 ml of THF/$H_2O$ (3:94) 40 ml was gradually added thereto. The obtained slurry was stirred for 1 hour under water-cooling, filtered and washed with water to give a crystal (type I). A crystal obtained from this Example showed the same date of each instrumental analysis of a crystal (type I) obtained from Example 13(1).

Example 13(3)

A Preparation of a Crystal (Type II) of 1-[5-(4-fluorobenzyl)furan-2-yl]-3-hydroxy-3-(1H-1,2,4-triazole-3-yl)propenone 2 g of 1-[5-(4-fluorobenzyl)furan-2-yl]-3-hydroxy-3-(1H-1,2,4-triazole-3-yl)propenone was dissolved in 600 ml of ethylacetate under heating. The solution was filtered, kept standing at room temperature and dried under usual pressure. The obtained crystal was washed with ethylacetate to give a crystal (type II). Judging from a data of single crystal X-ray diffraction, a crystal (type II) was a isomer having a structure of the formula:

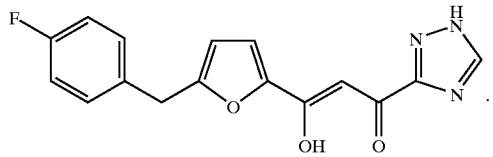

Crystal parameters of single crystal X-ray diffraction

| Unit cell constants: | a = 11.9003(7)Å |
|---|---|
| | b = 9.7183(5)Å |
| | c = 13.2617(8)Å |
| | α = 90.00° |
| | β = 109.450(4)° |
| | γ = 90.00° |
| | V = 1446.2(1)Å³ |
| | Z = 4 |
| Space group: P2₁/n | |
| Density: 1.439 g/cm³ | |

Diffraction angles (2θ) and intensities of main peaks of powder X-ray diffraction of a crystal (type II)

| Diffraction angle (2θ) | Intensity |
|---|---|
| 8.760 | 12805 |
| 19.600 | 8023 |
| 22.080 | 8473 |
| 23.760 | 20195 |
| 26.200 | 33235 |
| 27.580 | 11623 |
| 29.080 | 4913 |

Diffrential scanning calorimetry

| Peak (° C.) | ΔH (J/g) |
|---|---|
| 177.8 | 142.09 |
| 184.07 | 3.616 |

Example 13(4)

A Preparation of a Crystal (III) of 1-[5-(4-fluorobenzyl)furan-2-yl]-3-hydroxy-3-(1H-1,2,4-triazole-3-yl)propenone To 1g of 1-[5-(4-fluorobenzyl)furan-2-yl]-3-hydroxy-3-(1H-1,2,4-triazole-3-yl)propenone hydrochloride was added methanol (10 ml). After heating and stirring, methanol was concentrated under reduced pressure. Methanol (10 ml) was added to the residue and concentrated as well as the above again. Moreover, methanol (10 ml) was added to the residue and concentrated as well as the above again. The obtained slurry was kept standing overnight. A crystal was isolated and washed with methanol to give a crystal (type III).

Elementary analysis for $C_{16}H_{12}FN_3O_3$.

Calcd: C, 61.43; H, 3.86; F, 6.06; N, 13.41; Cl 0.00.

Found: C, 60.23; H, 3.98; F, 5.85; N, 13.38; Cl<0.10.

Diffraction angles (2θ) and intensities of main peaks of powder X-ray diffraction of a crystal (type III)

| Diffraction angle (2θ) | Intensity |
|---|---|
| 10.520 | 4020 |
| 13.860 | 10368 |
| 15.680 | 11768 |
| 18.160 | 4363 |
| 22.840 | 6723 |
| 26.180 | 6335 |
| 28.120 | 3928 |

-continued

| Diffrential scanning calorimetry | |
|---|---|
| Peak (° C.) | ΔH (J/g) |
| 130.8 | −9.116 |
| 186.13 | 144.3 |

An another process for the preparation of 2-acetyl-5-(4-fluorobenzyl)furan are described below.

Example 14(1)

A Process for the Preparation of 2-acetyl-5-(4-fluorobenzyl)furan (Another Route 1)

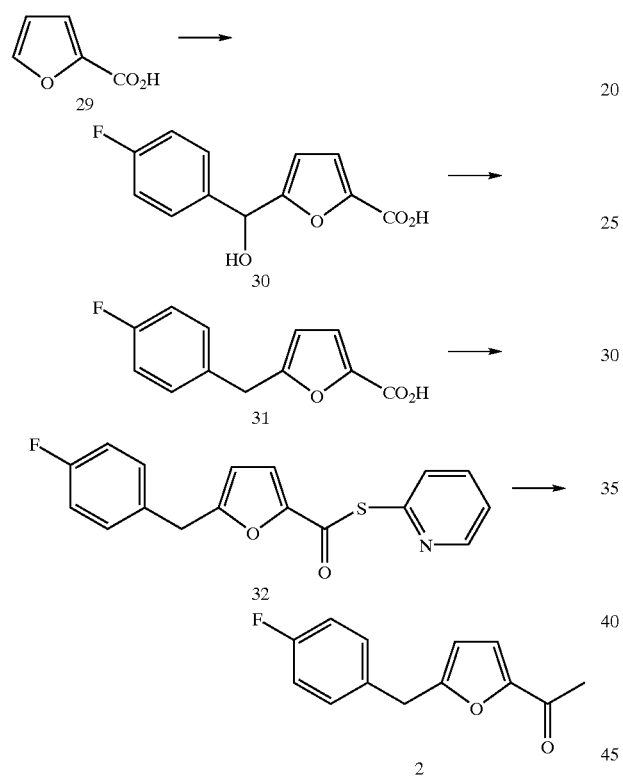

(1) 5.6 g (50 mmol) of 2-furancarboxylic acid was reacted with 6.8 g (55 mmol) of 4-fluoro benzasdehyde in accordance with Tetrahedron Letters, 1979, 51, p469. The obtained crude crystal was washed with isopropyl ether to give 8.1 g of 5-[[1-(4-fluorophenyl)-1-hydroxy]methyl]-furan-2-carboxylic acid. Yield: 69%. Mp: 139–140° C. (decomposition).

NMR(CDCl$_3$) δ 5.88(1H, s), 6.28(1H, d, J=3.6 Hz), 7.07(2H, t, J=8.7 Hz), 7.25(1H, d, J=3.6 Hz), 7.39–7.44(2H, m).

(2) 4.72 g (20 mmol) of the compound was reduced with 10.8 g (100 mmol) of trimethylchlorosilane and 15 g (100 mmol) of sodium iodide in accordance with Tetrahedron, 1995, 51, p11043 to give 3.52 g of 5-(4-fluorobenzyl)-furan-2-carboxylic acid as a crystal. Yield: 80%.

NMR(d6-DMSO) δ 4.05(2H, s), 6.31(1H, d, J=3.3 Hz), 7.12–7.18(3H, m), 7.27–7.32(2H, m), 12.9(1H, brs).

(3) 3.52 g (16 mmol) of the above compound was reacted with 4.2 g (19.2 mmol) of dipyridyldisulfide and 5.04 g (19.2 mmol) of triphenytphosphine in accordance with Bull. Chem. Soc. Japan., 1974, 47, p1777 to give 3.7 g of 5-(4-fluorobenzyl)-furan-2-carboxylic acid 2-pyridylthioester. Yield: 77%. Mp: 88–89° C.

NMR(CDCl$_3$) δ 4.04(2H, s), 6.15(1H, d, J=3.3 Hz), 7.03(2H, t, J=8.7 Hz), 7.22(1H, d, J=3.3 Hz), 7.22–7.26(2H, m), 7.29–7.34(1H, m), 7.70–7.79(2H, m), 8.63–8.66(1H, m).

(4) 3.7 g (12.4 mmol) of the above compound was reacted with 14 ml (1 M) of methyl magnesium bromide in accordance with Bull. Chem. Soc. Japan., 1974, 47, p1777 to give 2.7 g of 2-acetyl-5-(4-fluorobenzyl)-furan as an oil(2.7 g) quantitatively.

NMR(CDCl$_3$) δ 2.43(3H, s), 4.01(2H, s), 6.10(1H, d, J=3.6 Hz), 7.01(2H, t, J=9.0 Hz), 7.10(1H, d, J=3.6 Hz), 7.18–7.23(2H, m).

Example 14(2)

A process for the Preparation of 2-acetyl-5-(4-fluorobenzyl)furan (Another Route 2)

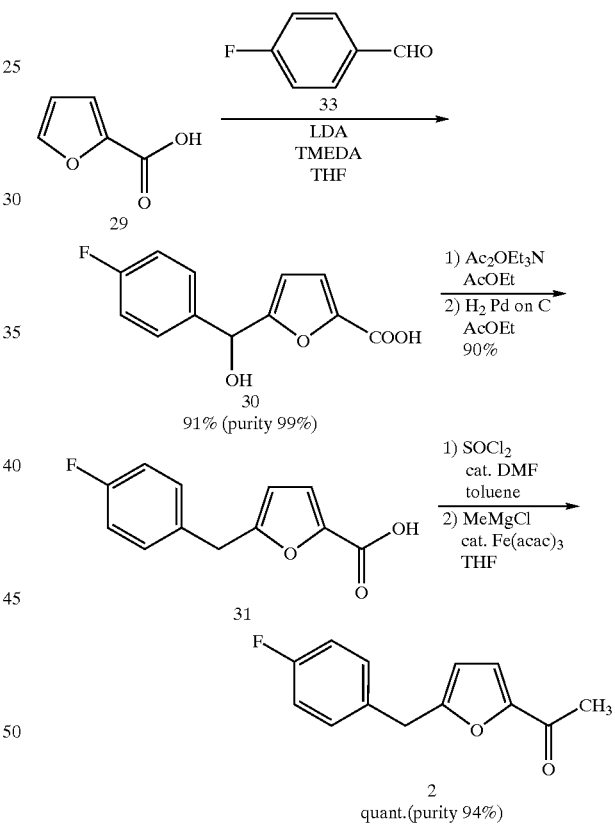

(1) LDA in 27.5 ml (25% solution, 30 mmol) of a mixed solution (THF/heptanelethylbenzene) was cooled to −50° C. and 7.5 ml (30 mmol) of tetramethylethylenediamine was added thereto. To the mixture was added with stirring under −45° C. for 25 minutes 2.24 g (20 mmol) of 2-furancarboxylic acid in 12 ml of THF. After stirring for 1 hour at −50° C., 40 ml of THF was added to the obtained suspension. 3.8 ml (35 mmol) of 4-fluorobenzaldehyde was immediately added thereto. The reaction temperature rose from 50 to −15° C. After stirring under ice-cooling for 30 minutes, 40 ml of water was added thereto. The organic layer was extracted with 1N sodium hydroxide aqueous solution. The obtained alkaline layer was washed with toluene, acidified with diluted hydrochloric acid and extracted with ethylacetate. The extract was washed with water, dried over anhydrous sodium sulfate and removed under reduced pressure. The obtained residue was crystallized from toluene and washed with cooled toluene to give a 4.29 g of hydroxy carboxylic acid. Yield: 91%.

(2) To a solution of 1.18 g (5 mmol) of hydroxy carboxylic acid and 1.52 g (15 mmol) of triethylamine in 15 ml of ethylacetate was added dropwise under ice-cooling a solution of 1.16 g (11.4 mmol) of acetic anhydride in 1 ml of ethylacetate. The solution was stirred under ice cooling for 30 minutes. 253 mg (2.5 mmol) of triethylamine and 180 mg of 10% palladium carbon were added thereto. The suspension was stirred at hydrogen atmosphere under usual pressure for 4.5 hours. The catalyst was filtered off. Dilute hydrochloric acid was added to the filtrate and extracted with ethylacetate. The extract was washed with water, dried over anhydrous magnesium sulfate and removed under reduced pressure. The obtained residue was crystallized from n-hexane and washed with n-hexane to give 991 mg of carboxylic acid. Yield: 90%.

(3) To a suspension of 1.00 g (4.54 mmol) of carboxylic acid in 5 ml of toluene were added 648 mg (5.44 mmol) of thionylchloride and 0.03 ml of DMF. The suspension was stirred at 80° C. for 1.5 hours. The solvent and excess of thionylchloride were removed under reduced pressure, mixed with 5 ml of toluene and removed under reduced pressure. To the obtained residue were added 10 ml of THF and 48 mg (0.12 mmol) of ironic acetyl acetonate (Fe(acac)$_3$). The solution was cooled at −20° C. To the solution was added dropwise for 10 minutes 1.75 ml (5.25 mmol) of 3M methyl magnesium chloride in THF with stirring at nitrogen atmosphere. The mixture was stirred at −20° C. for 30 minutes, mixed with diluted hydrochloric acid and extracted with toluene. The extract was washed with water, washed with sodium hydrogencarbonate aqueous solution, washed with water and removed under reduced pressure to give 1.02 g of 2-acetyl-5-(4-fluorobenzyl)furan. Yield: quantitative.

The following compounds are prepared in accordance with the present process.

1-[5-(4-Fluorobenzyl)furan-2-yl]-3-hydroxy-3-(2H-tetrazole-5-yl)-propenone

Mp: 121–123° C. Recrystallized from ether.

Elementary analysis for $C_{15}H_{11}FN_4O_3$; Calcd (%): C, 57.33; H, 3.53; N, 17.83; F, 6.04. Found (%): C, 57.25; H, 3.58; N, 17.53; F, 5.81.

NMR(d$_6$-DMSO) δ 4.16(2H, s), 6.51(1H, d, J=3.6 Hz), 7.05(1H, s), 7.18(2H, t, J=8.7 Hz), 7.32–7.38(2H, m), 7.65 (1H, d, J=3.6 Hz).

1-[5-(4-Fluorobenzyl)furan-2-yl]-3-hydroxy-3-(5-methyl-1H-[1,2,4]-triazole-3-yl)-propenone.

Mp: 179–182° C. Recrystallized from ethylacetate.

Elementary analysis for $C_{17}H_{14}FN_3O_3$; Calcd (%); C, 62.38; H, 4.31; N, 12.84; F, 5.80. Found (%): C, 62.29; H, 4.16; N, 11.65; F, 5.78.

NMR(d$_6$-DMSO) δ 2.43(3H, s), 4.14(2H, s), 6.46(1H, d, J=3.3 Hz), 6.88(1H, s), 7.15–7.20(2H, m), 7.31–7.36(2H, m), 7.49(1H, d, J=3.3 Hz), 14.3(1H, brs).

1-[5-(4-Chlorobenzyl)furan-2-yl]-3-hydroxy-3-(1H-[1,2,4]triazole-3-yl)-propenone Mp: 96–99° C. Recrystallized from ethanol.

Elementary analysis for $C_{16}H_{12}ClN_3O_3$; Calcd (%): C, 58.28; H, 3.67; N, 12.74; Cl, 10.75. Found (%): C, 58.16; H, 3.80; N, 12.40; Cl, 10.50.

NMR(d$_6$-DMSO) δ 4.16(2H, s), 6.49(1H, d, J=3.6 Hz), 6.93(1H, s), 7.30–7.43(4H, m), 7.52(1H, d, J=3.6 Hz), 8.75(1H, brs).

1-(5-Benzylfuran-2-yl)-3hydroxy-3-(1H-[1,2,4]triazole-3-yl)-propenone

Mp: 176–179° C. Recrystallized from ethylacetate.

Elementary analysis for $C_{16}H_{13}N_3O_3$ 0.15 $C_4H_8O_2$ Calcd (%): C, 64.63; H, 4.64; N, 13.62. Found (%): C, 64.41; H, 4.40; N, 13.42.

NMR(d$_6$-DMSO) δ 4.14(2H, s), 6.48(1H, d, J=3.6 Hz), 6.93(1H, s), 7.24–7.38(5H, m), 7.51(1H, d, J=3.6 Hz), 8.72(1H, brs), 14.7(1H, brs).

1-[[5-(4-Fluorobenzyl)-3-methyl]furan-2-yl]-3-hydroxy-3-(1H-[1,2,4]triazole-3-yl)-propenone.

Mp: 191–192° C. Recrystallized from ethylacetate.

Elementary analysis for $C_{17}H_{14}FN_3O_3$. Calcd (%): C, 62.38; H, 4.31; N, 12.84; F, 5.80. Found (%): C, 62.23; H, 4.29; N, 12.79; F, 5.79.

NMR(d$_6$-DMSO) δ 2.36(3H, s), 4.10(2H, s), 6.34(1H, s), 6.89(1H, s), 7.18(2H, t, J=9.0 Hz), 7.32–7.37(2H, m), 8.70 (1H, brs).

3-Hydroxy-1-[5-(4-methoxybenzyl)furan-2-yl]-3-(1H-[1,2,4]triazole-3-yl)-propenone.

Mp: 114–116° C. Recrystallized from ethylacetate.

Elementary analysis for $C_{17}H_{15}N_3O_4$; Calcd (%): C, 62.76; H, 4.65; N, 12.92. Found (%): C, 62.90; H, 4.57; N. 12.26.

NMR(d$_6$-DMSO) δ 3.73(3H, s), 4.07(2H, s), 6.44(1H, d, J=3.3 Hz), 6.91(2H, d, J=8.7 Hz), 6.92(1H, s), 7.22(2H, d, J=8.7 Hz), 7.50(1H, d, J=3.3 Hz), 8.77(1H, brs).

1-[5-(3-Fluorobenzyl)furan-2-yl]-3-hydroxy-3-(1H-[1,2,4]triazole-3-yl)-propenone.

Mp: 140–143° C. Recrystallized from ethanol.

Elementary analysis for $C_{16}H_{12}FN_3O_3$; Calcd (%): C, 61.34; H, 3.86; N, 13.41; F, 6.06. Found (%): C, 61.41; H, 3.84; N, 13.05; F, 5.97.

NMR(d$_6$-DMSO) δ 4.19(2H, s), 6.52(1H, d, J=3.3 Hz), 6.95(1H, s), 7.10–7.18(3H, m), 7.36–7.41(1H, m), 7.52(1H, d, J=3.3 Hz), 8.77(1H, brs), 14.7(1H, brs).

1-[5-(2-Fluorobenzyl)furan-2-yl]-3-hydroxy-3-(1H-[1,2,4]triazole-3-yl)-propenone Mp: 182–184° C. Recrystallized from ethanol/ether.

Elementary analysis for $C_{16}H_{12}FN_3O_3$; Calcd (%): C, 61.34; H, 3.86; N, 13.41; F, 6.06. Found (%): C, 61.47; H, 3.90; N, 13.04; F, 5.99.

NMR(d$_6$-DMSO) δ 4.18(2H, s), 6.46(1H, d, J=3.3 Hz), 6.94(1H, s), 7.17–7.26(2H, m), 7.32–7.40(2H, m), 7.51(1H, d, J=3.3 Hz), 8.79(1H, brs).

3-Hydroxy-1-[5-(4-methylbenzyl)furan-2-yl]-3-(1H-[1,2,4]triazole-3yl)-propenone.

Mp: 166–167° C. Recrystallized from ethylacetate.

Elementary analysis for $C_{17}H_{15}N_3O_3$ 0.1 $C_4H_8O_2$; Calcd (%): C, 65.69; H, 5.01; N, 13.21. Found (%): C, 65.45; H, 4.93; N, 13.37.

NMR(d$_6$-DMSO) δ 2.28(3H, s), 4.09(2H, s), 6.46(1H, d, J=3.6 Hz), 6.93(1H, s), 7.13–7.18(4H, m), 7.51(1H, d, J=3.6 Hz), 8.76(1H, brs), 14.7(1H, brs).

HIV-1 integrase inhibitory activities of propenone derivatives were examined in accordance with the following assay.

(1) Preparation of DNA Solutions.

Substrate DNA and target DNA, which sequences were indicated below, were synthesized by Amersham Pharmacia Biotech and dissolved in KTE buffer (composition: 100 mM KCl, 1 mM EDTA, 10 mM Tris-HCl (pH 7.6)) at concentration of 2 pmol/μl and 5 pmol/μl, respectively. The DNA solutions were annealed with each complement by slowly cooling after heating.

(Substrate DNA)

5'-Biotin-ACC CTT TTA GTC AGT GTG GAA AAT CTC TAG CAG T-3'

3'-GAA AAT CAG TCA CAC CTT TTA GAG ATC GTC A-5'

(Target DNA)

5'-TGA CCA AGG GCT AAT TCA CT-Dig-3'

3'-Dig-ACT GGT TCC CGA TTA AGT GA-5'

(2) Calculations of the Percent Inhibitions (the $IC_{50}$ Values of Test Compounds)

Streptavidin, obtained from Vector Laboratories, was dissolved in 0.1 M carbonate buffer (composition: 90 mM $Na_2CO_3$, 10 mM $NaHCO_3$) at concentration of 40 μg/ml. After coating each well of microtiter plates (obtained from NUNC) with 50 μl of the above solution at 4° C. over night, each well was washed twice with PBS (composition: 13.7 mM NaCl, 0.27 mM KCl, 0.43 mM $Na_2HPO_4$, 0.14 mM $KH_2PO_4$) and blocked with 300 μl of 1% skim milk in PBS for 30 min. Additionally, each well was washed twice with PBS and added 50 μl of substrate DNA solution (2 pmol/μl). The microtiter plates were kept at room temperature for 30 min. Then, each well was washed twice with PBS and once with $H_2O$.

Subsequently, in the each well prepared above were added 45 μl of the reaction buffer prepared from 12 μl of the buffer (composition: 150 mM MOPS (pH 7.2), 75 mM $MnCl_2$, 50 mM 2-mercaptoethanol, 25% glycerol, 500 μg/ml bovine serum albumin-fraction V), 1 μl of target DNA (5 pmol/μl), and 32 μl of the distilled water. Additionally, 6 μl of either a test compound in DMSO or DMSO for positive control (PC) was mixed with the above reaction buffer, then 9 μl of an integrase solution (30 pmol) was added and mixed well. In the well of negative control (NC) was added 9 μl of the integrase dilution buffer (composition: 20 mM MOPS (pH$_{7.2}$), 400 mM potassium glutamate, 1 mM EDTA, 0.1% NP-40, 20% glycerol, 1 mM DTT, 4M urea).

The microtiter plates were incubated at 30° C. for 1 hour. The reaction solution was removed and each well was washed twice with PBS. Subsequently, each well of the microtiter plates was filled with 100 μl of anti-digoxigenin antibody labeled with alkaline phosphatase (Sheep Fab fragment: obtained from Boehringer) and incubated at 30° C. for 1 hour. Then, each well was washed twice with 0.05% Tween20 in PBS and once with PBS. Next, 150 μl of the Alkaline phosphatase reaction buffer (composition: 10 mM p-Nitrophenylphosphate (obtained from Vector Laboratories), 5 mM $MgCl_2$, 100 mM NaCl, 100 mM Tris-HCl (pH 9.5))was added in each well. The microtiter plates were incubated at 30° C. for 2 hours and the reaction was terminated by the addition of 50 μl of 1 N NaOH solution. The optical density (OD) at 405 nm of each well was measured and the percent inhibition was determined by the following expression.

The percent inhibition (%)=100 [1-{(C abs.-NC abs.)/(PC abs.-NC abs.)}]

C abs.; the OD of the well of the compounds
NC abs.: the OD of the negative control (NC)
PC abs.: the OD of the positive control (PC)

When the percent inhibition (%) is X% at the concentration of x μg/ml and the percent inhibition (%) is Y% at the concentration of y μg/ml, one of which is more than 50% and the other is less than 50%, $IC_{50}$ can be determined by the following expression.

$$IC_{50}(\mu g/ml)=x-\{(X-50)(x-y)/(X-Y)\}$$

The $IC_{50}$ values, the concentration of the compounds at percent inhibition 50%, are shown in the following Table 1.

TABLE

| Compound No. | $IC_{50}$(μg/ml) |
| --- | --- |
| 22 | 0.53 |

INDUSTRIAL APPLICABILITY

2-Acyl-5-benzylfuran derivatives can be industrially and commercially prepared through Friedel Crafts reaction of 2-acylfuran derivatives. The present invention provides an industrial process for the preparation of 1,2,4-triazole-3-carboxylic acid ester derivatives. These processes can contribute to stable mass-production of an integrase inhibitor, an anti-HIV agent, or a compound (IV-1) or (IV-2).

What is claimed is:

1. A compound of the formula (IV-9):

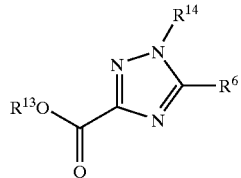

(IV-9)

wherein $R^6$ is hydrogen; $R^{13}$ is alkyl, a group of the formula: —$R^7$ wherein $R^7$ is trityl, optionally substituted sulfamoyl or alkoxymethyl, a group of the formula: C(OR$^8$)R$^9$—CHR$^{10}$R$^{11}$ wherein $R^8$ is alkyl; $R^9$, $R^{10}$ and $R^{11}$ each is independently hydrogen or alkyl; or $R^8$ and $R^{10}$ may be taken together to form alkylene, or hydroxymethyl; and $R^{14}$ is a group of the formula: —$R^7$ wherein $R^7$ is as defined above, a group of the formula: —C(OR$^8$)R$^9$—CHR$^{10}$R$^{11}$ wherein $R^8$, $R^9$, $R^{10}$ and $R^{11}$ are defined above, or hydroxymethyl, provided that a compound wherein $R^6$ is hydrogen; $R^{13}$ is methyl; and $R^{14}$ is trityl, a compound wherein $R^6$ is hydrogen; $R^{13}$ is methyl; and $R^{14}$ is tetrahydropyran-2-yl, and a compound wherein $R^6$ is hydrogen; $R^{13}$ is ethyl; and $R^{14}$ is trityl are excluded.

2. The compound according to claim 1 wherein $R^6$ is hydrogen; $R^{13}$ is methyl or ethyl; $R^{14}$ is tetrahydropyran-2-yl, hydroxymethyl, methoxymethyl, ethoxymethyl, N,N-dimethylsulfamoyl, (1-methoxy-1-methyl)ethyl, (1-ethoxy)ethyl, (1-ethoxy-1-methyl)ethyl, (1-n-propoxy)ethyl, (1-n-butoxy)ethyl or (1-isobutoxy)ethyl.

3. A process for the preparation of a compound of the formula (IV-9):

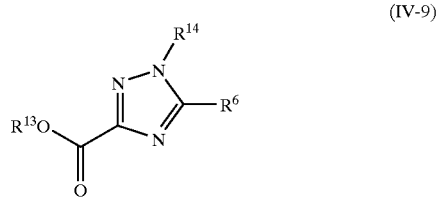

(IV-9)

wherein $R^6$, $R^{13}$ and $R^{14}$ are as defined in claim 1, provided that a compound wherein $R^6$ is hydrogen; $R^{13}$ is methyl; and $R^{14}$ is trityl, a compound wherein $R^6$ is hydrogen; $R^{13}$ is methyl; and $R^{14}$ is tetrahydropyran-2-yl, and a compound wherein $R^6$ is hydrogen; $R^{13}$ is ethyl; and $R^{14}$ is trityl are excluded, which comprises reacting a compound of the formula (IV-5-1):

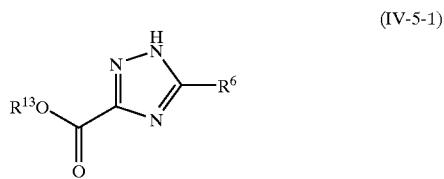

(IV-5-1)

wherein $R^6$ and $R^{13}$ are as defined in claim 1, with a compound of the formula: $R^7X$ wherein $R^7$ is as defined in claim 1; and X is halogen, a compound of the formula: $(R^8O)R^9C=CR^{10}R^{11}$ wherein $R^8$, $R^9$, $R^{10}$ and $R^{11}$ are as defined in claim 1, or formaldehyde.

4. A process of the preparation of a compound of the formula (IV-9):

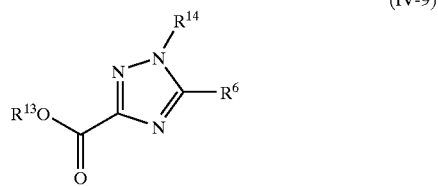

(IV-9)

wherein $R^6$, $R^{13}$ and $R^{14}$ are as defined in claim 1, provided that a compound wherein $R^6$ is hydrogen; $R^{13}$ is methyl; and $R^{14}$ is trityl, a compound wherein $R^6$ is hydrogen; $R^{13}$ is methyl; and $R^{14}$ is tetrahydropyran-2-yl, and a compound wherein $R^6$ is hydrogen; $R^{13}$ is ethyl; and $R^{14}$ is trityl are excluded, which comprises reacting a compound of the formula (IV-7):

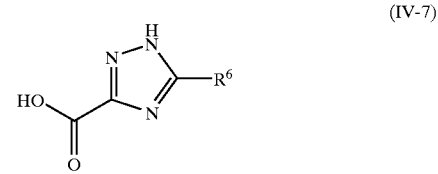

(IV-7)

wherein $R^6$ is as defined in claim 1, with a compound of the formula: $R^7X$ wherein $R^7$ is as defined in claim 1; and X is halogen, a compound of the formula: $(R^8O)R^9C=CR^{10}R^{11}$ wherein $R^8$, $R^9$, $R^{10}$ and $R^{11}$ are as defined in claim 1, or formaldehyde.

5. The process according to claim 3 or 4 which comprises reacting with a compound of the formula: $R^7X$ wherein $R^7$ is trityl.

6. The process according to claim 3 or 4 which comprises reacting with a compound of the formula: $(R^8O)R^9C=CR^{10}R^{11}$ wherein $R^8$ and $R^{10}$ are taken together to form trimethylene; and $R^9$ and $R^{11}$ each is hydrogen.

7. The process according to claim 3 or 4 which comprises reacting with a compound of the formula: $(R^8O)R^9C=CR^{10}R^{11}$ wherein $R^8$ and $R^9$ each is methyl; and $R^{10}$ and $R^{11}$ each is hydrogen.

8. A process for the preparation of a compound of the formula (VI-2):

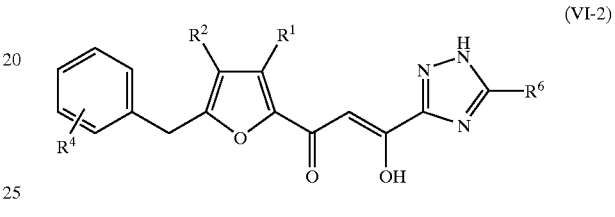

(VI-2)

wherein $R^1$, $R^2$ and $R^4$ each is independently hydrogen, optionally substituted alkyl, optionally substituted alkoxy or halogen; and $R^6$ is hydrogen, optionally substituted alkyl or optionally substituted aryl, which comprises reacting a compound of the formula (IV-9):

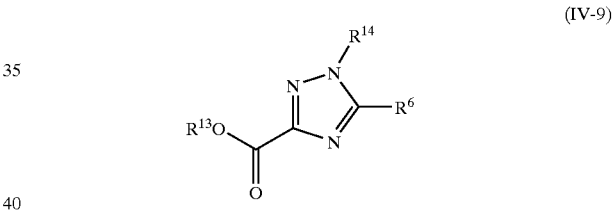

(IV-9)

wherein $R^6$, $R^{13}$ and $R^{14}$ are as defined in claim 1, provided that a compound wherein $R^6$ is hydrogen; $R^{13}$ is methyl; and $R^{14}$ is trityl, a compound wherein $R^6$ is hydrogen; $R^{13}$ is methyl; and $R^{14}$ is tetrahydropyran-2-yl, and a compound wherein $R^6$ is hydrogen; $R^{13}$ is ethyl; and $R^{14}$ is trityl are excluded, with a compound of the formula (III-2):

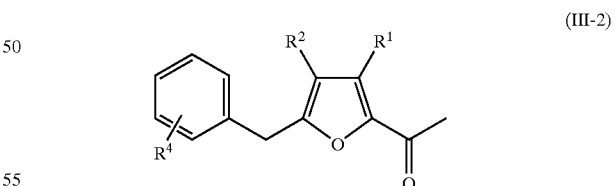

(III-2)

wherein $R^1$, $R^2$ and $R^4$ are as defined above, and deprotecting $R^{14}$.

9. The process according to claim 8 wherein $R^1$, $R^2$ and $R^6$ each is hydrogen; and $R^4$ is halogen.

* * * * *